US010738047B2

(12) United States Patent
Doroshow et al.

(10) Patent No.: US 10,738,047 B2
(45) Date of Patent: Aug. 11, 2020

(54) IODONIUM ANALOGS AS INHIBITORS OF NADPH OXIDASES AND OTHER FLAVIN DEHYDROGENASES; FORMULATIONS THEREOF; AND USES THEREOF

(71) Applicants: THE UNITED STATES OF AMERICA as represented by THE SECRETARY, DEPARTMENT OF HEALTH, Bethesda, MD (US); STARKS ASSOCIATES INC., Buffalo, NY (US)

(72) Inventors: James Halpern Doroshow, Bethesda, MD (US); Prabhakar Risbood, Germantown, MD (US); Jiamo Lu, Potomac, MD (US); Krishnendu Roy, Gaithersburg, MD (US); Charles T. Kane, Jr., East Amherst, NY (US); Md Tafazzal Hossain, Amherst, NY (US)

(73) Assignees: THE UNITED STATES OF AMERICA, AS REPRESENTED BY THE SECRETARY, DEPARTMENT OF HEALTH, Bethesda, MD (US); STARKS ASSOCIATES INC., Buffalo, NY (US)

( * ) Notice: Subject to any disclaimer, the term of this patent is extended or adjusted under 35 U.S.C. 154(b) by 15 days.

(21) Appl. No.: 16/160,599

(22) Filed: Oct. 15, 2018

(65) Prior Publication Data
US 2019/0048001 A1 Feb. 14, 2019

Related U.S. Application Data

(63) Continuation of application No. 15/302,566, filed as application No. PCT/US2015/024445 on Apr. 6, 2015, now Pat. No. 10,131,659.

(60) Provisional application No. 61/976,362, filed on Apr. 7, 2014.

(51) Int. Cl.
| | |
|---|---|
| *C07D 471/04* | (2006.01) |
| *A61K 31/381* | (2006.01) |
| *A61K 31/4745* | (2006.01) |
| *C07D 333/28* | (2006.01) |
| *C07D 409/12* | (2006.01) |
| *C07C 43/225* | (2006.01) |
| *C07C 205/12* | (2006.01) |
| *C07C 233/15* | (2006.01) |
| *C07D 347/00* | (2006.01) |
| *C07D 409/14* | (2006.01) |

(52) U.S. Cl.
CPC .......... *C07D 471/04* (2013.01); *A61K 31/381* (2013.01); *A61K 31/4745* (2013.01); *C07C 43/225* (2013.01); *C07C 205/12* (2013.01); *C07C 233/15* (2013.01); *C07D 333/28* (2013.01); *C07D 347/00* (2013.01); *C07D 409/12* (2013.01); *C07D 409/14* (2013.01)

(58) Field of Classification Search
None
See application file for complete search history.

(56) References Cited

U.S. PATENT DOCUMENTS

| 3,763,187 A | 10/1973 | Moyle |
| 4,096,267 A | 6/1978 | Crageo, Jr. et al. |
| 6,086,794 A | 7/2000 | Nobutoki et al. |
| 2017/0029424 A1 | 2/2017 | Doroshow et al. |

FOREIGN PATENT DOCUMENTS

| CN | 102617546 A | 8/2012 |
| CN | 103172612 B | 7/2015 |
| DE | 2166953 A1 | 6/1987 |
| EP | 0225478 A1 | 6/1987 |
| GB | 1496167 | 10/1975 |
| JP | 62122324 A | 10/1977 |
| JP | 2006232801 | 7/2006 |
| KR | 20120003832 A | 1/2012 |
| KR | 1011435750000 | 4/2012 |
| KR | 1011894850000 | 10/2012 |

OTHER PUBLICATIONS

Hua et al., CAS SciFinder abstract (CAPLUS Acc. No. 1996:633902) of Chemical Research in Chinese Universities (1996), 12(3), pp. 309-312.*
Chen et al., CAS SciFinder abstract (CAPLUS Acc. No. 1990:469986) of Sciences in China, Series B: Chemistry, Life Sciences & Earth Sciences (1989), 32(8), pp. 918-926).*
Zheng et al., CAS SciFinder abstract (CAPLUS Acc. No. 1990:151270) of Chinese Science Bulletin (1989), 34(18), pp. 1559-1562.*
Hua et al., Chemical Research in Chinese Universities (1996), 12(3), pp. 309-312.*
Chen et al., Science in China, Series B: Chemistry, Life Sciences & Earth Sciences (1989), 32(8), pp. 918-926.*
Zheng et al., Chinese Science Bulletin (1989), 34(18), pp. 1559-1562.*
An et al.; "Design of oligothiophene-based tetrazoles for laser-triggered photoclick chemistry in living cells"; Chemical Communications (Cambridge, United Kingdom) (2013), 49(85), 9920-9922.
Barton et al.; "Biphenylenes: The Synthesis of 1-Nitro- and 1-Amino-biphenylene"; Journal of the Chemical Society [Section] C: Organic, 1967, Issue: 21, pp. 2097-2099.
Beringer et al., "Diaryliodonium Salts. VII. 2,2'-Dithienyl- and Phenyl-2-thienyliodonium Salts." J. Am. Chem. Soc; 1958;80:4279.
Beringer et al., "Iodonium Salts Containing Heterocyclic Iodine"; J. Org. Chem.; 1965; 30:1141.
Blatchly et al., "Biphenylenes. Part VII. Synthese of 2,3-Dimethoxybiphenylene"; J. Chem. Soc.;1962:5085.
CAS SciFinder Compound list 101-200 [retrieved on Jul. 14, 2016] Retrieved from CAS SciFinder American Chemical Society 2016 using https://scifinder.cas.org/scifinder.
CAS SciFinder Compound list 1-100 [retrieved on Jul. 14, 2016] Retrieved from CAS SciFinder American Chemical Society 2016 using https://scifinder.cas.org/scifinder.

(Continued)

*Primary Examiner* — Brian J Davis
(74) *Attorney, Agent, or Firm* — Cantor Colburn LLP

(57) ABSTRACT

Disclosed herein are novel iodonium analogs having anti-cancer and anti-inflammatory activity.

19 Claims, 3 Drawing Sheets

(56) References Cited

OTHER PUBLICATIONS

CAS SciFinder Compound list 201-300 [retrieved on Jul. 14, 2016] Retrieved from CAS SciFinder American Chemical Society 2016 using https://scifinder.cas.org/scifinder.

CAS SciFinder Compound list 301-361 [retrieved on Jul. 14, 2016] Retrieved from CAS SciFinder American Chemical Society 2016 using https://scifinder.cas.org/scifinder.

D'Auria et al., "Photochemical Reactivity of Aromatic and Heteroaromatic Nitroderivatives in the Presence of Arylalkenes." Tetrahedron; 1996;52:14253.

Ding, "Imporved Synthesis of 3,6 Diaminobipheny 1 Fused Iodine-Containing Heterocycles";Lanzhou Xuebao, Ziran Kexueban;1984;20;1:169.

Dohi et al.; "Unusual ipso Substitution of Biaryliodonium Bromides Initiated by a Single-Electron-Transfer Oxidizing Process"; Angewandte Chemie, International Edition (2010), 49(19), 3334-3337, S3334/1-S3334/12.

Dohi, et al.; "Fluoroalcohols: versatile solvents in hypervalent iodine chemistry and syntheses of diaryliodonium(III) salts"; Tetrahedron (2010), 66(31), 5775-5785.

Doroshow et al., "Antiproliferative mechanisms of action of the flavin dehydrogenase inhibitors diphenylene iodonium and di-2-thienyliodonium based on molecular profiling of the nci-60 human tumor cell panel." Biochemical Pharmacology;2012;83:1195-1207.

Doroshow et al., "Prevention of Duxorubicin-Induced Killing of MCF-7 Human Breast Cancer Cells by Oxygen Radical Scavengers and Iron Chelating Agents";Biochem Biophys. Res. Commun;1986;135:330-335.

Doroshow et al.; "Effects of iodonium-class flavin dehydrogenase inhibitors on growth reactive oxygen production, cell cycle progression, nadph oxidase 1 levels, and gene expression in human colon cancer cells and xenografts." Free radical biology and medicine;2013;57:162-175.

Enguehard et al., "Reactivity of 3-Iodoimidazo[1,2-a]pyridines Using a Suzuki-Type Cross-Coupling Reaction"; J. Org. Chem.; 2000;65:6572.

Hancock et al. "The use of diphenylene iodonium and its analogs to investigate the role of the NADPH oxidase in the tumoricidal activity of macrophages in vitro" Free Radical Biology & Medicine, vol. 11, Issue: 1, pp. 25-9, 1991.

Huang et al. "Heterocyclic compounds containing iodine. IV. Synthesis of 3,6-dialkylaminodiphenyl heterocyclic compounds" Kexue Tongbao (Chinese Edition), Issue: 11, pp. 47-8, Journal, 1963.

Huang, "Synthesis of 3,6 Dihalodibenzo-cycloidonium Salts"; Lanzhou Daxue Xuebao, Ziran Kexueban;1984;4:67.

Hwang, "Studies on Heterocyclic Compounds containing Iodine II.";Huaxue Xuebao;1957;23:438-With English Abstract.

Hwang, "Studies on Heterocyclic Compounds Containing Iodine. I. The Preparation of 3,6-Dinitrodibenzopyriodonium Salts (III) and Their Properties"; Sci. Sin. (Engl. Ed.);1957;6:123.

International Search Report; International Application No. PCT/US2015/024445; International Filing Date Apr. 6, 2015;dated Jun. 8, 2015; 8 pages.

Jacquet et al., "NADPH oxidase (NOX) isoforms are inhibited by celastrol with a dual mode of action"; Brit J. Pharmacology;2011;164: 507-520.

Johnson et al., "Synthesis of the Three Isomeric Ortho-Substituted Phenylthienyl Benzoic Acids"; J. Org. Chem.;1976;41:1320.

Kazmierczak et al., "A Short-Cut Synthesis of Diaryliodonium Bromides Followed by Oxidative Anion Metatheses." Synthesis;1995;1027.

Kehrmann et al., "Uber Acetylierung von Derivaten des Diphenylamins mit Essigsaure-anhydrid und Zinkchloid"; Helv. Chim. Acta.;1926;2:673.

Kellogg et al., "Acid-Catalyzed Brominations, Deuterations, Rearrangements, and Debrominations of Thiophenes under Mild Conditions"; J. Org. Chem.;1968;33:2902.

Koser et al.; "[Hydroxy(tosyloxy)iodo]benzene, a Versatile Reagent for the Mild Oxidation of Aryl Iodides at the Iodine Atom"; Journal of Organic Chemistry (1980), 45(8), 1542-3.

Liang et al. "Stereoselective Heck-type cross-coupling reactions of iodine heterocyclic compounds with olefins" Tetrahedron, vol. 56, Issue: 19, pp. 2961-2965, 2000.

Lu, Jiamo et al: "Characterization of potent and selective iodonium-class inhibitors of NADPH oxidases", Biochemical Pharmacology, vol. 143, Nov. 1, 2017 (Nov. 1, 2017), pp. 25-38, XP055471534, US ISSN: 0006-2952, DOI: 10.1016/j.bcp.2017.07.007.

Margida et al.; "Direct Condensation of [Hydroxy(tosyloxy)iodo]arenes with Thiophenes. A Convenient, Mild Synthesis of Aryl(2-thienyl)iodonium Tosylates"; Journal of Organic Chemistry (1984), 49(19), 3643-6.

McKillop et al., "Further Functional Group Oxidations Using Sodium Perborate." Tetrahedron 1989;45:3299.

Menkissogle-Spiroudi, et al., "Hypervalent iodine compounds as potentialantibacterial agents against ice nucleation active (ina) pseudomonas syringae." J. Agric Food Chem;2001;49:3746-3752.

Moriarty et al., "Novel Penta-fluorophenyl Hypervalent Iodine Reagents." Tetrahedron Lett.;1987:877.

Moulton, et al., "The inhibition of flavoproteins by phenoxaiodonium, a new iodonium analogue." European Journal of Pharmacology; 2000;401:115-200.

Nabana et al., "Reactivities of Novel [Hydroxy-(tosyloxy)iodo)arenes and [Hydroxy(phosphoryloxy)iodo)arenes for -Tosyloxylation and -Phosphoryloxylation of Ketones." J. Org. Chem;2002;67:4362.

O'Donnell et al. "Studies on the inhibitory mechanism of iodomium compounds with special reference to neutrophil NADPH oxidase" Biochemical Journal, vol. 290, Issue: 1, pp. 41-9, 1993.

Onys'ko et al.; "Cascade iodination-fluorination synthesis of 2-fluorothiophene and 5-fluoro-2-thienyliodonium salts"; Journal of Fluorine Chemistry (2009), 130(5), 501-504.

Smith et al., "The Synthesis of Heterocyclic Compounds from Aryl Azides. III. Some Six-membered Rings and Some Azidobiaryls"; J. Am. Chem. Soc.;1953;75:6335.

Stang, et al.; "Preparation of bis(Heteroaryl)iodonium Salts via an Iodonium Transfer Reaction Between Di(cyano) iodonium Triflate and Organostannes"; Journal of Heterocyclic Chemistry (1992), 29(4), 815-818.

Stuehr et al. "Inhibition of macrophage and endothelial cell nitric oxide synthase by diphenyleneiodonium and its analogs" FASEB Journal, vol. 5, Issue: 1, pp. 98-103, 1991.

Togo et al., "Preparation and Reactivities of Novel (Diacetoxyiodo)arenes Bearing Heteroaromatics" J. Org. Chem;2000;65:8391.

Wang et al. "Action of iodo-heterocyclic compounds on the heart blood vessels" Kexue Tongbao (Chinese Edition), Issue: 10, pp. 57-8, Journal, 1963.

Wasylewsky et al., "Preparation of 4-Nitrodiphenyleneiodonium Chloride"; J. Am. Chem. Soc.; 1950;72:1038.

Written Opinion of the International Searching Authority; International Application No. PCT/US2015/024445; International Filing Date Apr. 6, 2016; dated Jun. 8, 2015; 12 pages.

Zhang, et al., "Synthesis of the 8-Oxo-Diquino (5,6-b;6,6-e)-Pyriodonium Compound"; Yingyong Xuaxue;1986;1;4:48.

Zhdankin, Science of Synthesis (2007), 31a, 161-233.

Zheng Rongliang et al: "Relationships between structure & effect of iodium heterocycle compounds on tumor cells DNA, RNA & protein syntheses in vitro", CN Sci Bulletin, Sci CN Press & Springer, CN, V34, N18, Jan. 1, 1989, 1559-62, XP009505111, ISSN:1001-6538.

Zhu et al.; "One-Pot Synthesis of Diaryliodonium Salts Using Toluenesulfonic Acid: A Fast Entry to Electron-Rich Diaryliodonium Tosylates and Triflates"; Synlett (2008), (4), 592-596.

\* cited by examiner

FIG. 4A, 4B, and 4C

IODONIUM ANALOGS AS INHIBITORS OF NADPH OXIDASES AND OTHER FLAVIN DEHYDROGENASES; FORMULATIONS THEREOF; AND USES THEREOF

CROSS REFERENCE TO RELATED APPLICATIONS

This application is a continuation application of U.S. application Ser. No. 15/302,566 filed Oct. 7, 2016, which is a National Stage application of PCT/US2015/024445, filed Apr. 6, 2015, which claims the benefit of U.S. Provisional Application No. 61/976,362, filed Apr. 7, 2014, each of which is incorporated by reference in its entirety herein.

FIELD OF THE DISCLOSURE

The present disclosure is directed to iodonium analogs useful as inhibitors of NADPH oxidases and other flavin dehydrogenases.

BACKGROUND

Reactive oxygen species (ROS) are molecules produced as by-products of cellular metabolism that are often generated by flavin dehydrogenase enzymes, including the NADPH oxidase family of proteins and others; they play a critical role in the control of the growth of human cancers as well as the body's inflammatory response to both infectious and non-infectious stimuli. It has been demonstrated that some human tumors, including colorectal and pancreatic cancers and pre-cancers, ovarian cancers, melanomas, and others express these oxidase proteins at high level, and that the ROS they produce are essential for the proliferation of these cells. NADPH oxidases are also expressed by cells that produce an immune response against tumors or other stimuli as well as cells of the cardiovascular system; when the oxidase activity of these pro-inflammatory immune or vascular cells is excessive, pathological damage to normal tissues may ensue.

SUMMARY

Drugs that effectively interfere with the production of ROS by the NADPH oxidases are not widely available. Thus, there remains a need in the art for new NADPH oxidase inhibitor compounds.

In an embodiment, a compound according to Formula I . . .

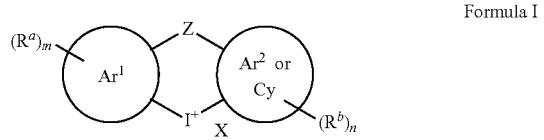

Formula I wherein
X is an anion;
$Ar^1$ and $Ar^2$ are each independently an aryl or a heteroaryl group;
Cy is a cycloalkyl, a heterocycloalkyl, or a cycloalkenyl;
Z is absent, a bond, O, S, $CH_2$, —C(=O)—, or $NR^c$ where $R^c$ is hydrogen, $C_1$-$C_6$alkyl, $C_1$-$C_6$haloalkyl, or $C_2$-$C_6$alkanoyl;

each instance of $R^a$ and $R^b$ are independently a halogen, hydroxyl, amino, nitro, cyano, optionally substituted $C_1$-$C_6$alkyl, $C_2$-$C_6$alkenyl, $C_3$-$C_7$cycloalkyl, —COOR$^d$, —CHO, —N(R$^e$)$_2$, —CON(R$^e$)$_2$, $C_1$-$C_6$alkoxy, $C_2$-$C_6$alkanoyl, $C_1$-$C_6$haloalkyl, $C_1$-$C_6$haloalkoxy, optionally substituted aryl, or optionally substituted heteroaryl, where each optionally substituted $C_1$-$C_6$alkyl can independently be substituted with hydroxyl, halogen, amino, nitro, cyano, —COOR$^d$, —CHO, —N(R$^e$)$_2$, —CON(R$^e$)$_2$, $C_1$-$C_3$alkoxy, $C_1$-$C_3$haloalkoxy, $C_2$-$C_6$alkanoyl, —NHCO(CH$_2$)$_{1-2}$N(R$^e$)$_2$, where each $R^d$ is independently hydrogen or $C_1$-$C_3$ alkyl,
where each $R^e$ is independently hydrogen, $C_1$-$C_6$alkyl, $C_2$-$C_6$alkanoyl, $C_1$-$C_6$haloalkyl, or fluorenylmethyloxycarbonyl ("Fmoc"), where each optionally substituted aryl and optionally substituted heteroaryl can independently be substituted with halogen, hydroxyl, amino, nitro, cyano, $C_1$-$C_6$alkyl, $C_2$-$C_6$alkenyl, $C_3$-$C_7$cycloalkyl, $C_1$-$C_6$haloalkyl, —COOR$^d$, —CHO, —N(R$^e$)$_2$, —CON(R$^e$)$_2$, $C_1$-$C_3$alkoxy, $C_1$-$C_3$haloalkoxy, $C_2$-$C_6$alkanoyl, —NHCO(CH$_2$)$_{1-2}$N(R$^e$)$_2$;

m is 0, 1, 2, 3, or 4; and
n is 0, 1, 2, 3, or 4;
with the proviso that
when $Ar^1$ and $Ar^2$ are both phenyl and Z is absent or a bond, then m or n is not 0, and
when $Ar^1$ and $Ar^2$ are both thienyl and Z is absent, then m or n is not 0.

In an embodiment, a pharmaceutical composition comprises a compound of Formula I, or any of its subformula, and optionally a pharmaceutically acceptable carrier.

In an embodiment, a method for treating or preventing a cancer comprises administering a therapeutically effective amount of a compound of Formula I, or any of its subformula, to a human patient or a non-human mammal suffering from a cancer.

In an embodiment, a method for treating or preventing tumor growth comprises administering a therapeutically effective amount of a compound of Formula I, or any of its subformula, to a human patient or a non-human mammal in need of such treatment.

In an embodiment, a method for treating or preventing an inflammatory condition comprises administering a therapeutically effective amount of a compound of Formula I, or any of its subformula, to a human patient or a non-human mammal in need of such treatment.

In an embodiment, a method of treating or preventing a cancer, inhibiting or preventing tumor growth, or treating or preventing an inflammatory condition, comprises administering a therapeutically effective amount of a compound of Formula Ib to a human patient or a non-human mammal

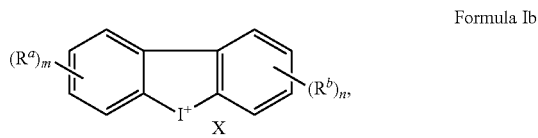

Formula Ib wherein X is an anion;
each instance of $R^a$ and $R^b$ are independently a halogen, hydroxyl, amino, nitro, cyano, optionally substituted $C_1$-$C_6$alkyl, $C_2$-$C_6$alkenyl, $C_3$-$C_7$cycloalkyl, —COOR$^d$, —CHO, —N(R$^e$)$_2$, —CON(R$^e$)$_2$, $C_1$-$C_6$alkoxy, $C_2$-$C_6$alkanoyl, $C_1$-$C_6$haloalkyl, $C_1$-$C_6$haloalkoxy, optionally substituted aryl, or optionally substituted heteroaryl, where each optionally substituted $C_1$-$C_6$alkyl can independently be substituted with hydroxyl, halogen, amino, nitro, cyano, —COOR$^d$, —CHO, —N(R$^e$)$_2$, —CON(R$^e$)$_2$, $C_1$-$C_3$alkoxy, $C_1$-$C_3$haloalkoxy, $C_2$-$C_6$alkanoyl, —NHCO(CH$_2$)$_{1-2}$N(R$^e$)$_2$, where each R$^d$ is independently hydrogen or $C_1$-$C_3$ alkyl, where each W is independently hydrogen, $C_1$-$C_6$alkyl, $C_2$-$C_6$alkanoyl, $C_1$-$C_6$haloalkyl, or fluorenylmethyloxycarbonyl ("Fmoc"), where each optionally substituted aryl and optionally substituted heteroaryl can independently be substituted with halogen, hydroxyl, amino, nitro, cyano, $C_1$-$C_6$alkyl, $C_2$-$C_6$alkenyl, $C_3$-$C_7$cycloalkyl, $C_1$-$C_6$haloalkyl, —COOR$^d$, —CHO, —N(R$^e$)$_2$, —CON(R$^e$)$_2$, $C_1$-$C_3$alkoxy, $C_1$-$C_3$haloalkoxy, $C_2$-$C_6$alkanoyl, —NHCO(CH$_2$)$_{1-2}$N(R$^e$)$_2$;

m is 0, 1, 2, 3, or 4; and n is 0, 1, 2, 3, or 4;

with the proviso that m and n are not both 0.

DETAILED DESCRIPTION

Figure 1:
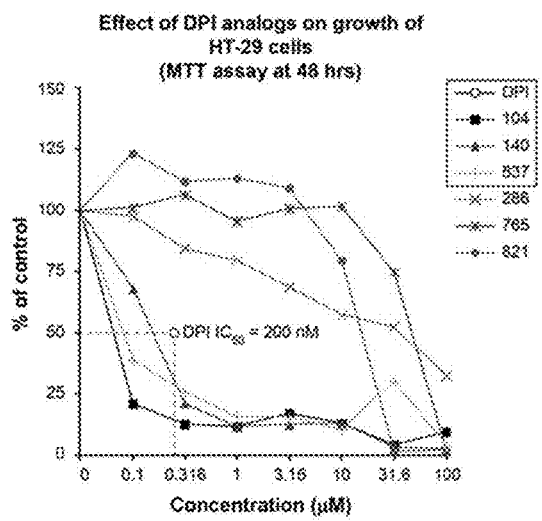
FIG. 1 illustrates the effect of DPI analogs on growth of HT-29 human colon cancer cells by MTT assay: 48 hr.
Figure 2:
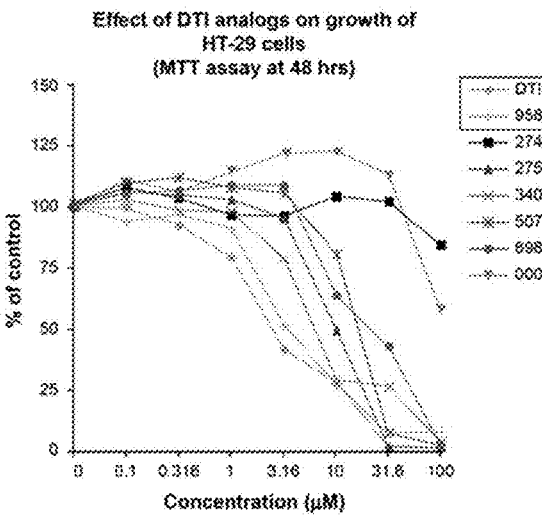
FIG. 2 illustrates the effect of DTI analogs on growth of HT-29 human colon cancer cells by MTT assay: 48 hr.

The NADPH oxidase (NOX) gene family (NOX1-5 and Duox1/2) plays an important role in host defense and the development of inflammation-induced carcinogenesis. Members of the NOX family are distributed in an organ-specific fashion in human tumors. Evidence suggests that NOX1 and DUOX2 are overexpressed in many human colonic adenocarcinomas. Further, many human cancers express both NOX5 and DUOX2 isoforms. These cancers include colon cancer, prostate cancer, breast cancer, and squamous lung cancer in addition to ovarian cancer, melanoma, Non-Hodgkin lymphoma and Glioblastoma Multiforme. Thus, there is a potential major role for the NOX family as targets for cancer therapy.

It has been found that two iodonium-class NOX inhibitors, diphenyleneiodonium (DPI) and di-2-thienyliodonium (DTI), block NOX-dependent reactive oxygen species (ROS) formation, NOX1 mRNA expression, and growth of human colon cancer cells in vitro and in vivo (Free Rad. Biol. Med. 57: 162-165, 2013).

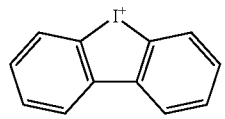

diphenyleneiodonium ("DPI")

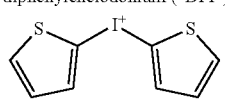

di-2-thienyliodonium ("DTI")

Disclosed herein is a series of novel iodonium analog compounds that effectively interfere with the production of ROS by the NADPH oxidases. These new compounds are more potent or more specific inhibitors of tumor cell growth and/or inflammation-related signaling than DPI and DTI. Additionally, several of the analogs possess improved solubility in water, aqueous systems and water miscible organic solvents (e.g. ethanol, dimethyl sulfoxide, etc.).

The iodonium analog compounds include those compounds according to Formula I:

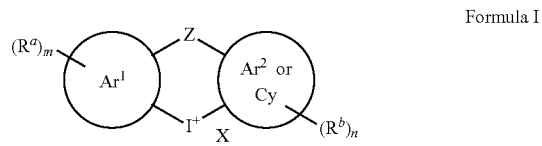

Formula I wherein

X is an anion;

Ar$^1$ and Ar$^2$ are each independently an aryl or a heteroaryl group;

Cy is a cycloalkyl, a heterocycloalkyl, or a cycloalkenyl;

Z is absent, a bond, O, S, CH$_2$, —C(=O)—, or NW where R$^e$ is hydrogen, $C_1$-$C_6$alkyl, $C_1$-$C_6$haloalkyl, or $C_2$-$C_6$alkanoyl;

each instance of R$^a$ and R$^b$ are independently a halogen, hydroxyl, amino, nitro, cyano, optionally substituted $C_1$-$C_6$alkyl, $C_2$-$C_6$alkenyl, $C_3$-$C_7$cycloalkyl, —COOR$^d$, —CHO, —N(R$^e$)$_2$, —CON(R$^e$)$_2$, $C_1$-$C_6$alkoxy, $C_2$-$C_6$alkanoyl, $C_1$-$C_6$haloalkyl, $C_1$-$C_6$haloalkoxy, optionally substituted aryl, or optionally substituted heteroaryl, where each optionally substituted $C_1$-$C_6$alkyl can independently be substituted with hydroxyl, halogen, amino, nitro, cyano, —COOR$^d$, —CHO, —N(R$^e$)$_2$, —CON(R$^e$)$_2$, $C_1$-$C_3$alkoxy, $C_1$-$C_3$haloalkoxy, $C_2$-$C_6$alkanoyl, or —NHCO(CH$_2$)$_{1-2}$N(R$^e$)$_2$, where each R$^d$ is independently hydrogen or $C_1$-$C_3$ alkyl, where each R$^e$ is independently hydrogen, $C_1$-$C_6$alkyl, $C_2$-$C_6$alkanoyl, $C_1$-$C_6$haloalkyl, or fluorenylmethyloxycarbonyl ("Fmoc"), where each optionally substituted aryl and optionally substituted heteroaryl can independently be substituted with halogen, hydroxyl, amino, nitro, cyano, $C_1$-$C_6$alkyl, $C_2$-$C_6$alkenyl, $C_3$-$C_7$cycloalkyl, $C_1$-$C_6$haloalkyl, —COOR$^d$, —CHO, —N(R$^e$)$_2$, —CON(R$^e$)$_2$, $C_1$-$C_3$alkoxy, $C_1$-$C_3$haloalkoxy, $C_2$-$C_6$alkanoyl, —NHCO(CH$_2$)$_{1-2}$N(R$^e$)$_2$;

m is 0, 1, 2, 3, or 4; and
n is 0, 1, 2, 3, or 4;
with the proviso that
when Ar$^1$ and Ar$^2$ are both phenyl and Z is absent or a bond, then m or n is not 0, and
when Ar$^1$ and Ar$^2$ are both thienyl and Z is absent, then m or n is not 0.

In an embodiment, X is a halide, an alkyl sulfonate, an aryl sulfonate, a phosphate, or a nitrate. The halide can be chloride, bromide, or iodide. The alkyl sulfonate can be CH$_3$SO$_3$—, C$_2$H$_5$SO$_3$—, or CF$_3$SO$_3$—. The aryl sulfonate can be 4-CH$_3$C$_6$H$_4$SO$_3$— or C$_6$H$_5$SO$_3$—.

In an embodiment, Ar$^1$ and Ar$^2$ are each independently an aryl such as phenyl, naphthyl, bi-phenyl, and the like.

In an embodiment, Ar$^1$ and Ar$^2$ are each independently a heteroaryl group such as benzofuranyl, benzothiazolyl, coumarinyl, furanyl, imidazolyl, imidazo[1,2-a]pyridine, indolyl, isoquinolinyl, isoxazolyl, 3-methylisoxazole, oxazolyl, pyrazinyl, pyridyl, pyrimidinyl, pyrrolyl, quinazolinyl, quinolinyl, thiazolyl, triazinyl, thienyl, and the like.

In an embodiment, Cy is cyclohexanone or a 3-hydroxycyclohex-2-enone.

In an embodiment, Ar$^1$ is a heteroaryl such as thienyl and Ar$^2$ is a heteroaryl such as thienyl, further substituted by a R$^a$ group, a R$^b$ group, or a combination thereof; and Z is absent.

In an embodiment, Ar$^1$ is an aryl such as phenyl and Ar$^2$ is a heteroaryl such as thienyl, further substituted by a R$^a$ group, a R$^b$ group, or a combination thereof; and Z is absent.

In an embodiment, Ar$^1$ and Ar$^2$ are both quinolinyl; and Z is absent or O.

In an embodiment, Ar$^1$ and Ar$^2$ are both phenyl substituted by a R$^a$ group, a R$^b$ group, or a combination thereof; and Z is absent, a bond, O, S, CH$_2$, or NR$^c$ where R$^c$ is C$_2$-C$_6$alkanoyl.

In an embodiment, Ar$^1$ is an aryl such as phenyl and Ar$^2$ is a heteroaryl such as imidazo[1,2-a]pyridine, further substituted by a R$^a$ group, a R$^b$ group or a combination thereof; and Z is absent. In an embodiment, the R$^b$ group is optionally substituted phenyl.

In an embodiment, Ar$^1$ is a heteroaryl such as thienyl and Ar$^2$ is a heteroaryl such as imidazo[1,2-a]pyridine, further substituted by a R$^a$ group, a R$^b$ group, or a combination thereof; and Z is absent. In an embodiment, the R$^b$ group is optionally substituted phenyl.

In an embodiment, Ar$^1$ is a heteroaryl such as thienyl and Cy is optionally substituted 3-hydroxycyclohex-2-enone, optionally substituted 3-hydroxy-5,5-dimethylcyclohex-2-enone, or 3-hydroxy-5,5-dimethyl-4-(3-methylisoxazol-5-yl)cyclohex-2-enone; and Z is absent.

In addition to compounds of Formula I as described above, this disclosure also includes Formulae Ia to Ii which are subgeneric compounds of Formula I, that carry any combination of the variable definitions set forth below that result in a stable compound.

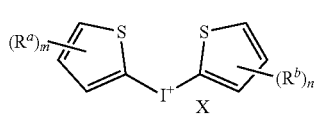
Formula Ia

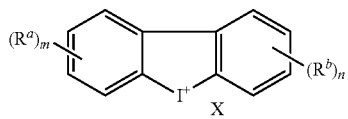
Formula Ib

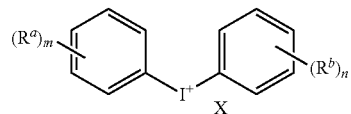
Formula Ic

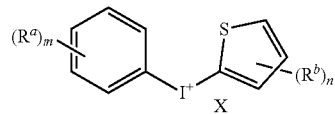
Formula Id

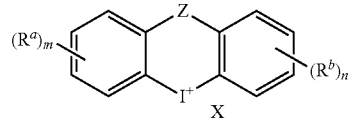
Formula Ie

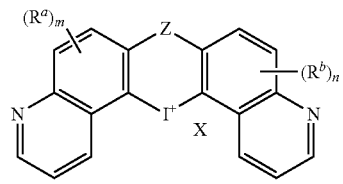
Formula If

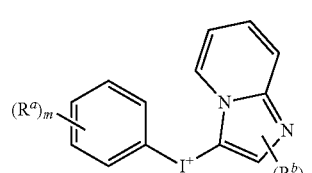
Formula Ig

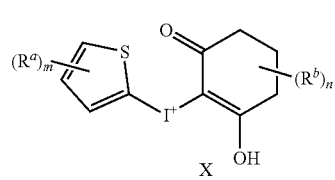
Formula Ih

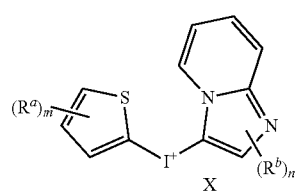
Formula Ii

The groups X, Z, R$^a$, R$^b$, m and n of Formulae Ia to Ii carry the same definitions as defined above for Formula I.

Also included in this disclosure are compounds of Formula I, specifically those compounds set out in Table 1 herein.

The compounds are described using standard nomenclature. Unless defined otherwise, all technical and scientific terms used herein have the same meaning as is commonly understood by one of skill in the art to which this disclosure belongs.

The term "Formula I", as used herein, encompasses all compounds that satisfy Formula I, including any enantiomers, racemates and stereoisomers, as well as all pharmaceutically acceptable hydrates and solvates of such compounds. The phrase "a compound of Formula I" includes all subgeneric groups of Formula I including Formula Ia to Ti, and so forth, as well as all forms of such compounds, including hydrates and solvates, unless clearly contraindicated by the context in which this phrase is used.

Formula I includes all subformulae thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example, a chiral HPLC column.

Where a compound exists in various tautomeric forms, the compound is not limited to any one of the specific tautomers, but rather includes all tautomeric forms.

All isotopes of atoms occurring in the present compounds are contemplated. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $R^a$, $R^b$, X, Z, $Ar^1$, etc. Unless otherwise specified, each variable within such a formula is defined independently of other variables. Thus, if a group is said to be substituted, e.g., with 0-2 $R^a$, then the group may be substituted with up to two $R^a$ groups and $R^a$ at each occurrence is selected independently from the definition of $R^a$. Also, combinations of substituents and/or variables are permissible only if such combinations result in stable compounds.

The term "active agent", as used herein, means a compound (including a compound of Formula I), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then hydrates and solvates of the compound, crystalline forms, non-crystalline forms, and any polymorphs of the compound are included. All forms are contemplated herein regardless of the methods used to obtain them.

A dash ("-") that is not between two letters or symbols is used to indicate a point of attachment for a substituent. For example, —(CH$_2$)C$_3$-C$_8$cycloalkyl is attached through the carbon of the methylene (CH$_2$) group.

"Alkanoyl" is an alkyl group as defined herein, covalently bound to the group it substitutes by a keto (—(C=O)—) bridge. Alkanoyl groups have the indicated number of carbon atoms, with the carbon of the keto group being included in the numbered carbon atoms. For example a C$_2$alkanoyl group is an acetyl group having the formula CH$_3$(C=O)—.

The term "alkyl", as used herein, means a branched or straight chain saturated aliphatic hydrocarbon group having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_6$alkyl, $C_1$-$C_4$alkyl, and $C_1$-$C_2$alkyl. When $C_0$-$C_n$ alkyl is used herein in conjunction with another group, for example, (cycloalkyl)$C_0$-$C_4$alkyl, the indicated group, in this case cycloalkyl, is either directly bound by a single covalent bond ($C_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

The term "alkenyl", as used herein, means straight and branched hydrocarbon chains comprising one or more unsaturated carbon-carbon bonds, which may occur in any stable point along the chain. Alkenyl groups described herein typically have from 2 to about 12 carbon atoms. Exemplary alkenyl groups are lower alkenyl groups, those alkenyl groups having from 2 to about 8 carbon atoms, e.g. $C_2$-$C_8$, $C_2$-$C_6$, and $C_2$-$C_4$ alkenyl groups. Examples of alkenyl groups include ethenyl, propenyl, and butenyl groups.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

The term "cycloalkyl", as used herein, indicates a saturated hydrocarbon ring group, having only carbon ring atoms and having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

The term "cycloalkenyl", as used herein, means a saturated hydrocarbon ring group, comprising one or more unsaturated carbon-carbon bonds, which may occur in any stable point of the ring, and having the specified number of carbon atoms. Monocyclic cycloalkenyl groups typically have from 3 to about 8 carbon ring atoms or from 3 to 7 (3, 4, 5, 6, or 7) carbon ring atoms. Cycloalkenyl substituents may be pendant from a substituted nitrogen or carbon atom, or a substituted carbon atom that may have two substituents may have a cycloalkenyl group, which is attached as a spiro group. Examples of cycloalkenyl groups include cyclopropenyl, cyclobutenyl, cyclopentenyl, or cyclohexenyl as well as bridged or caged saturated ring groups such as norbornene.

The term "heterocycloalkyl", as used herein, indicates a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

"Alkoxy" is an alkyl group as defined herein attached through an oxygen bridge (oxygen of an alcohol radical).

"Haloalkoxy" is a haloalkyl group as defined herein attached through an oxygen bridge (oxygen of an alcohol radical).

The term "aryl", as used herein, means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Bicyclic aryl groups may be further substituted with carbon or non-carbon atoms or groups. Bicyclic aryl groups may contain two fused aromatic rings (naphthyl) or an aromatic ring fused to a 5- to 7-membered non-aromatic cyclic group that optionally contains 1 or 2 heteroatoms independently chosen from N, O, and S, for example, a 3,4-methylenedioxy-phenyl group. Aryl groups include, for example, phenyl, naphthyl, including 1-naphthyl and 2-naphthyl, and bi-phenyl.

The term "mono- or bicyclic heteroaryl", as used herein, indicates a stable 5-to 7-membered monocyclic or 7- to 10-membered bicyclic heterocyclic ring which contains at least 1 aromatic ring that contains from 1 to 4, or specifically from 1 to 3, heteroatoms chosen from N, O, and S, with remaining ring atoms being carbon. When the total number of S and O atoms in the heteroaryl group exceeds 1, theses heteroatoms are not adjacent to one another. Specifically, the total number of S and O atoms in the heteroaryl group is not more than 2, more specifically the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. In certain embodiments 5- to 6-membered heteroaryl groups are used. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Halo" or "halogen" is any of fluoro, chloro, bromo, and iodo.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example, a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on a "substituted" or "optionally substituted" position include, but are not limited to, halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

Also provided are pharmaceutical compositions comprising a compound of Formula I, or any of its subformula, and optionally a pharmaceutically acceptable carrier. Such pharmaceutical compositions may contain a compound of Formula I, or any of its subformula, as the only active agent or may contain a combination of a compound of Formula I and another pharmaceutically active agent.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. Exemplary dosage form is a solid oral dosage form.

The term "pharmaceutical compositions", as used herein, are compositions comprising at least one active agent, such as a compound of Formula I or any of its subformulae, and optionally at least one other substance, such as a carrier. Pharmaceutical compositions meet the U.S. FDA's GMP (good manufacturing practice) standards for human or non-human drugs. The pharmaceutical compositions can be formulated into a dosage form.

The term "carrier", as used herein, applied to pharmaceutical compositions refers to a diluent, excipient, or vehicle with which an active compound is provided.

The term "patient", as used herein, is a human or non-human animal in need of medical treatment. Medical treatment can include treatment of an existing condition, such as a disease or disorder, prophylactic or preventative treatment, or diagnostic treatment. In some embodiments the patient is a human patient.

The term "providing", as used herein, means giving, administering, selling, distributing, transferring (for profit or not), manufacturing, compounding, or dispensing.

The term "providing a compound of Formula I with at least one additional active agent", as used herein, means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment" or "treating" means providing an active compound to a patient in an amount sufficient to measurably reduce any symptom of a disease or disorder for which the active compound is provided. The compounds of the present disclosure find use in the treatment of tumors that depend on ROS to proliferate, for the prevention of precancerous lesions that require ROS-induced genetic instability to progress to full-fledged malignancy, and for the treatment of pathological inflammatory conditions that are caused or exacerbated by the ROS generated by cells of the immune or vascular systems.

The term "therapeutically effective amount" of a compound of Formula I, or a related formula, means an amount effective, when administered to a human or non-human patient, to provide a therapeutic benefit such as an amelioration of symptoms, e.g., an amount effective to decrease the symptoms of a cancer or an inflammatory condition. Thus a therapeutically effective amount of a compound is also an amount sufficient significantly reduce the indicia of the disease or condition being treated. A significant reduction is any detectable negative change that is statistically significant in a standard parametric test of statistical significance, such as Student's t-test, in which $p<0.05$.

The compounds can be administered as the neat chemical, or administered as a pharmaceutical composition. Accordingly, an embodiment provides pharmaceutical compositions comprising a compound of Formula I, or any of its subformula, together with a pharmaceutically acceptable carrier. The pharmaceutical composition may contain a compound of Formula I or any of its subformula as the only active agent, or may contain one or more additional active agents.

The compounds may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the compound of Formula I.

The pharmaceutical compositions can be formulated for oral administration. These compositions contain between 0.1 and 99 weight percent ("wt. %") of a compound of Formula I, or its subformula, and specifically at least about 5 wt. %. Some embodiments contain from about 25 wt. % to about 50 wt. % or from about 5 wt. % to about 75 wt. % of a compound of Formula I, or its subformula.

The pharmaceutical composition can be formulated in a package comprising the pharmaceutical composition of Formula I, or its subformula, in a container and further comprising instructions for using the composition in order to elicit a therapeutic effect in a patient or to treat a patient suffering from cancer, an inflammatory condition, and the like.

The compounds of Formula I, as well as pharmaceutical compositions comprising the compounds, are useful for treating or preventing cancer, including a method of inhibiting or preventing tumor growth in vivo. The method of treating or preventing cancer or inhibiting or preventing a cancerous tumor growth comprises providing to a patient an effective amount of a compound of Formula I. In an embodiment the patient is a mammal, and more specifically a human. The disclosure also provides methods of treating non-human patients such as companion animals, e.g. cats, dogs, and livestock animals. An effective amount of a pharmaceutical composition may be an amount sufficient to inhibit the progression cancer or a cancerous tumor; or cause an inhibition of a cancerous tumor growth.

An effective amount of a compound or pharmaceutical composition described herein will also provide a sufficient concentration of a compound of Formula I when administered to a patient. A sufficient concentration is a concentration of the compound in the patient's body necessary to prevent or combat the disorder. Such an amount may be ascertained experimentally, for example by assaying blood concentration of the compound, or theoretically, by calculating bioavailability.

Methods of treatment include providing certain dosage amounts of a compound of Formula I to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

The iodonium compounds of Formula I possess antineoplastic activity. Not wishing to be bound by theory, it appears the antineoplastic activity is related, in part, to the compounds' direct inhibitory effects on the NADPH oxidase family of flavin dehydrogenases. Other signal transduction pathways, particularly those related to the inflammatory response, innate immunity, and the cardiovascular system, are also affected by the NADPH oxidases and a variety of flavin dehydrogenases. It is well known that inflammatory responses in immune cells and the vasculature are altered by flavoprotein inhibition. In an embodiment, the compounds of Formula I, as well as pharmaceutical compositions comprising the compounds, can be used to treat anti-inflammatory (as well as anti-oxidase) actions that may be important for the control of chronic inflammatory conditions, including precancerous lesions such as chronic pancreatitis (related to Dual oxidase 2), pulmonary and hepatic fibrosis (known to be NADPH oxidase related), and inflammatory bowel disease (recently related to NADPH oxidase 1 and Dual oxidase expression); as well as inflammation-related cardiovascular diseases and diabetes (associated with NADPH oxidases 1 and 4).

In an embodiment, a method of treating or preventing a cancer comprises administering a therapeutically effective amount of a compound of Formula I to a human patient or a non-human mammal suffering from a cancer.

In an embodiment, a method of inhibiting or preventing tumor growth comprises administering a therapeutically effective amount of a compound of Formula I to a human patient or a non-human mammal in need of such treatment.

The compounds of Formula I may be used to treat cancers and effect inhibition of tumors, including cancerous tumors. In certain embodiments, the patient is suffering from a cell proliferative disorder or disease. The cell proliferative disorder can be cancer, tumor (cancerous or benign), neoplasm, neovascularization, or melanoma. Cancers for treatment include both solid and disseminated cancers. Exemplary solid cancers (tumors) that may be treated by the methods provided herein include e.g. cancers of the colon, kidney (renal cell), lung (e.g. squamous), brain (e.g. Glioblastoma Multiforme), prostate, breast, ovarian, pancreatic, or skin including malignant melanoma. Exemplary disseminated cancers include leukemias or lymphoma (e.g. Non-Hodgkin).

In an embodiment, a method for treating or preventing an inflammatory condition comprises administering a therapeutically effective amount of a compound of Formula I to human patient or non-human mammal in need of such treatment, as well as pharmaceutical compositions comprising the compounds.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A compound of Formula I may be administered singularly (i.e., sole active agent of a regime) to treat or prevent diseases and conditions such as undesired cell proliferation, cancer, and/or tumor growth or may be administered in combination with another active agent. One or more compounds of Formula I may be administered in coordination with a regime of one or more other chemotherapeutic agents such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of Formula I include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer (e.g. therapeutic antibodies directed against CD20 (e.g. rituximab) or against VEGF (e.g. bevacizumab)).

Methods of treatment provided herein are also useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

In an embodiment, a method of treating or preventing a cancer, inhibiting or preventing tumor growth, or treating or preventing an inflammatory condition, comprises
administering a therapeutically effective amount of a compound of Formula Ib to a human patient or a non-human mammal suffering from a cancer

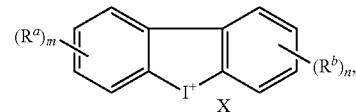

wherein X is an anion;
each instance of $R^a$ and $R^b$ are independently a halogen, hydroxyl, amino, nitro, cyano, optionally substituted $C_1$-$C_6$alkyl, $C_2$-$C_6$alkenyl, $C_3$-$C_7$cycloalkyl, —COOR$^d$, —CHO, —N(R$^e$)$_2$, —CON(R$^e$)$_2$, $C_1$-$C_6$alkoxy, $C_2$-$C_6$alkanoyl, $C_1$-$C_6$haloalkyl, $C_1$-$C_6$haloalkoxy, optionally substituted aryl, or optionally substituted heteroaryl,
where each optionally substituted $C_1$-$C_6$alkyl can independently be substituted with hydroxyl, halogen, amino, nitro, cyano, —COOR$^d$, —CHO, —N(R$^e$)$_2$, —CON(R$^e$)$_2$, $C_1$-$C_3$alkoxy, $C_1$-$C_3$haloalkoxy, $C_2$-$C_6$alkanoyl, —NHCO(CH$_2$)$_{1-2}$N(R$^e$)$_2$,
where each R$^d$ is independently hydrogen or $C_1$-$C_3$ alkyl,
where each R$^e$ is independently hydrogen, $C_1$-$C_6$alkyl, $C_2$-$C_6$alkanoyl, $C_1$-$C_6$haloalkyl, or fluorenylmethyloxycarbonyl ("Fmoc"),
where each optionally substituted aryl and optionally substituted heteroaryl can independently be substituted with halogen, hydroxyl, amino, nitro, cyano, $C_1$-$C_6$alkyl, $C_2$-$C_6$alkenyl, $C_3$-$C_7$cycloalkyl, $C_1$-$C_6$haloalkyl, —COOR$^d$, —CHO, —N(R$^e$)$_2$, —CON(R$^e$)$_2$, $C_1$-$C_3$alkoxy, $C_1$-$C_3$haloalkoxy, $C_2$-$C_6$alkanoyl, —NHCO(CH$_2$)$_{1-2}$N(R$^e$)$_2$;
m is 0, 1, 2, 3, or 4; and
n is 0, 1, 2, 3, or 4;
with the proviso that m and n are not both 0. Further within this embodiment, the cancer is colon cancer, kidney cancer (renal cell), melanoma, leukemia, prostate cancer, breast cancer, squamous lung cancer, ovarian cancer, pancreatic cancer, Non-Hodgkin lymphoma, or Glioblastoma Multiforme. Still further with this embodiment, each instance of $R^a$ and $R^b$ are independently nitro; m is 0, 1, or 2; and n is 0, 1, or 2. Further within this embodiment, the compound of Formula Ib is a halide, alkyl sulfonate, aryl sulfonate, phosphate, or nitrate salt of 3-nitro-dibenz[b,d] iodolium; 3,7-dinitro-dibenziodolium; or 1,9-dinitrodibenzo[b,d]iodolium.

This invention is further illustrated by the following examples that should not be construed as limiting.

EXAMPLES

Example 1

A series of iodonium analog compounds according to Formula I were prepared as shown in Table 1 along with comparative compounds DTI (compound 1) and DPI (compound 13). Scheme 1 provides a generalized synthetic route to substituted DTI analogs. Scheme 2 provides a generalized synthetic route to substituted DPI analogs.

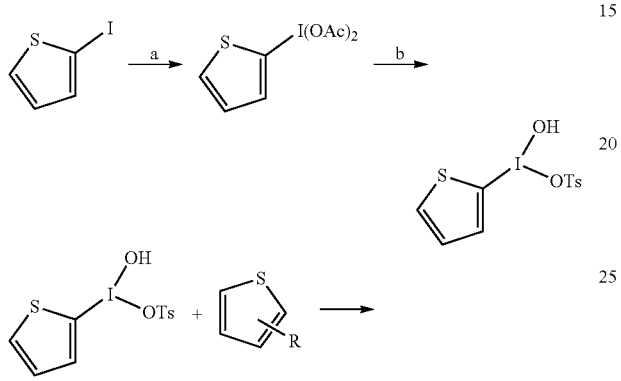

a. NaBo3·H2O, HOAc;
b. 4-CH$_3$C$_6$H$_4$SO$_3$H

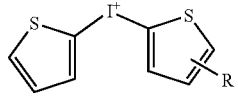

a. I$_2$, KIO$_3$, H$_2$SO$_4$;
b. KI

Solubility of several DTI analogs was improved in water, aqueous systems and water miscible solvents (e.g. ethanol, dimethyl sulfoxide, etc.) by the use of p-toluene sulfonate salts. Likewise, the solubility of several DPI analogs was improved when formed as a chloride salt.

TABLE 1

| Compound Description | | NSC Number | Ref.* |
|---|---|---|---|
| 1 (DTI) | R = H, X = Cl$^-$<br>di-2-thienyliodonium chloride | 734426 | 1,2 |
| 2 | R = H, X = I$^-$<br>di-2-thienyliodonium iodide | 734427 | 1,2 |
| 3 | R = H, X = CF$_3$SO$_3^-$<br>di-2-thienyliodonium triflate | 734958 | 1,2,3 |
| 4 | R = H, X = CH$_3$SO$_3^-$<br>Iodonium, di-2-thienyl-, salt with methanesulfonic acid (1:1) | 734959 | |
| 5 | R = H, X = C$_2$H$_5$SO$_3^-$<br>Iodonium, di-2-thienyl-, salt with with ethanesulfonic acid (1:1) | 734960 | |
| 6 | R = —NO$_2$, X = CH$_3$SO$_3^-$<br>Iodonium, (5-nitro-2-thienyl)-2-thienyl-, salt with methane-sulfonic acid (1:1) | 735202 | 4,5 |
| 7 | R = —CH$_2$CON(CH$_3$)$_2$, X = 4-CH$_3$C$_6$H$_4$SO$_3^-$<br>Iodonium, [5-[2-(dimethylamino)-2-oxoethyl]-2-thienyl]-2-thienyl-, salt with 4-methylbenzenesulfonic acid (1:1) | 748274 | |
| 8 | R = I, X = 4-CH$_3$C$_6$H$_4$SO$_3^-$<br>Iodonium, (5-iodo-2-thienyl)-2-thienyl-, salt with 4-methyl-benzenesulfonic acid (1:1) | 748275 | |
| 9 | R = —CH$_2$OH, X = 4-CH$_3$C$_6$H$_4$SO$_3^-$<br>Iodonium, [5-(hydroxymethyl)-2-thienyl]-2-thienyl-, salt with 4-methylbenzenesulfonic acid (1:1) | 748340 | |
| 10 | R = —CH$_2$CH$_2$NHCOCH$_3$, X = 4-CH$_3$C$_6$H$_4$SO$_3^-$<br>Iodonium, [5-[2-(acetylamino)-ethyl]-2-thienyl]-2-thienyl-, salt with 4-methylbenzene-sulfonic acid (1:1) | 748430 | |
| 11 | R = -2-(2-pyridinyl-6-carboxaldehyde), X = 4-CH$_3$C$_6$H$_4$SO$_3^-$ | 748698 | |

TABLE 1-continued

| Compound | Description | NSC Number | Ref.* |
|---|---|---|---|
| | Iodonium, [5-(2-formyl-6-pyridinyl)-2-thienyl]-2-thienyl-, salt with 4-methylbenzenesulfonic acid (1:1) | | |
| 12 | R = CH$_2$NH-Fmoc, X = 4-CH$_3$C$_6$H$_4$SO$_3^-$ Iodonium, [5-[[(9-fluorenyl-methoxycarbonyl)amino]methyl]-2-thienyl]-2-thienyl-, salt with p-toluenesulfonic acid (1:1) | 736096 | |

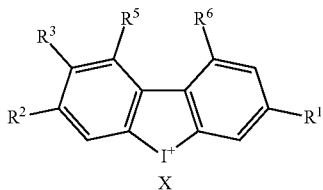

| Compound | Description | NSC Number | Ref.* |
|---|---|---|---|
| 13 (DPI) | R$^1$ = R$^2$ = R$^3$ = R$^5$ = R$^6$ = H X = Cl$^-$ Diphenyleneiodonium chloride | 735294 | |
| 14 | R$^1$ = —NO$_2$, R$^2$ = R$^3$ = R$^5$ = R$^6$ = H, X = Cl$^-$ CAS no. 46502-38-9 Dibenz[b,d]iodolium, 3-nitro-,chloride | 734428 | 10 |
| 15 | R$^1$ = R$^2$ = —NO$_2$, R$^3$ = R$^5$ = R$^6$ = H, X = Br$^-$ CAS # 46980-64-7 Dibenziodolium, 3,7-dinitro-, bromide | 737392 | 11 |
| 16 | R$^1$ = R$^2$ = Br, R$^3$ = R$^5$ = R$^6$ = H, X = Br$^-$ CAS # 96686-21-4 Dibenziodolium, 3,7-dibromo-,bromide | 740104 | 16 |
| 17 | R$^1$ = R$^2$ = —NH$_2$, R$^3$ = R$^5$ = R$^6$ = H, X = Cl$^-$ CAS # 92734-15-1 Dibenziodolium, 3,7-diamino-,chloride | 737695 | 15 |
| 18 | R$^1$ = R$^2$ = —NH$_2$, R$^3$ = R$^5$ = R$^6$ = H, X = CH$_3$SO$_3^-$ Dibenziodolium, 3,7-diamino-, methanesulfonate | 740543 | |
| 19 | R$^1$ = R$^2$ = —N(CH$_3$)$_2$, R$^3$ = R$^5$ = R$^6$ = H, X = I$^-$ Dibenziodolium, 3,7-bis(dimethylamino)-, Iodide | 737544 | 13,14 |
| 20 | R$^1$ = R$^2$ = —N(CH$_3$)$_2$, R$^3$ = R$^5$ = R$^6$ = H, X = CH$_3$SO$_3^-$ Dibenziodolium, 3,7-bis(dimethyl-amino)-, methanesulfonate | 743401 | |
| 21 | R$^1$ = —CO$_2$CH$_3$, R$^2$ = R$^3$ = R$^5$ = R$^6$ = H, X = 4-CH$_3$C$_6$H$_4$SO$_3^-$ Dibenz[b,d]iodolium, 3-(methoxy-carbonyl)-, salt with 4-methyl-benzenesulfonic acid (1:1) | 751140 | |
| 22 | R$^1$ = R$^2$ = —CH$_2$N(CH$_3$)$_2$, R$^3$ = R$^5$ = R$^6$ = H, X = I$^-$, Dibenziodolium, 3,7-bis[(di-methylamino)methyl]-, iodide hydroiodide | 742461 | |
| 23 | R$^1$ = R$^2$ = —NHCOCH$_2$N(CH$_3$)$_2$, R$^3$ = R$^5$ = R$^6$ = H, X = Cl$^-$ Dibenziodolium, 3,7-bis[[[(di-methylamino)methyl]carbonyl]-amino]-, chloride (~94:6 bisamide:monoamide) | 742193 | |
| 24 | R$^1$ = R$^2$ = —CH$_2$N(CH$_3$)$_2$, R$^3$ = R$^5$ = R$^6$ = H, X = I$^-$ Dibenziodolium, 3,7-bis[(di-methylamino)methyl]-, iodide | 742837 | |
| 25 | R$^1$ = R$^5$ = R$^6$ = H, R$^2$ = R$^3$ = —OCH$_3$, X = I$^-$ CAS # 96955-63-4 2,3-Dimethoxydibenziodolium iodide | 737755 | 12 |
| 49 | R$^5$ = R$^6$ = —NO$_2$, R$^1$ = R$^2$ = R$^3$ = H, X = Br$^-$ 1,9-dinitrodibenzo[b,d]iodolium bromide | 521 | |

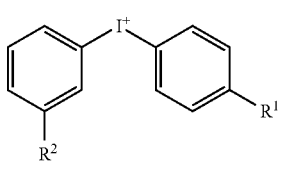

| Compound | Description | NSC Number | Ref.* |
|---|---|---|---|
| 26 | R$^1$ = —OCH$_3$, R$^2$ = H, X = 4-CH$_3$C$_6$H$_4$SO$_3^-$ CAS # 27126-77-8 Iodonium, (4-methoxyphenyl)-phenyl-, salt with 4-methyl-benzenesulfonic acid (1:1) | 736286 | 8 |

TABLE 1-continued

| | Compound Description | NSC Number | Ref.* |
|---|---|---|---|
| 27 | $R^1$ = —OCH$_3$, $R^2$ = —NO$_2$, X = 4-CH$_3$C$_6$H$_4$SO$_3^-$<br>CAS # 110441-18-4 (p-Methoxyphenyl)(m-nitrophenyl)-iodonium p-toluenesulfonate | 736287 | 6,7,8,9 |
| 28 | $R^1$ = —NHCOCH$_3$, $R^2$ = H, X = 4-CH$_3$C$_6$H$_4$SO$_3^-$<br>CAS # 187799-26-4 Iodonium, [4-(acetylamino)-phenyl]phenyl-, salt with 4-methylbenzenesulfonic acid (1:1) | 736321 | 8 |
| 29 | $R^1$ = —NHCOCH$_3$, $R^2$ = —NO$_2$, X = 4-CH$_3$C$_6$H$_4$SO$_3^-$<br>CAS # 110170-45-8 Iodonium, [4-(acetylamino)-phenyl](3-nitrophenyl)-, salt with 4-methylbenzene-sulfonic acid (1:1) | 736322 | 6,7,8,9 |

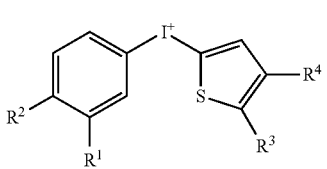

X

| | | | |
|---|---|---|---|
| 30 | $R^1$ = $R^2$ = $R^3$ = $R^4$ = H, X = 4-CH$_3$C$_6$H$_4$SO$_3^-$<br>CAS # 91228-44-3 Iodonium, phenyl-2-thienyl-, salt with 4-methylbenzenesulfonic acid (1:1) | 736289 | 8 |
| 31 | $R^1$ = —NO$_2$, $R^2$ = $R^3$ = $R^4$ = H, X = 4-CH$_3$C$_6$H$_4$SO$_3^-$<br>Iodonium, 3-nitrophenyl-2-thienyl-, salt with 4-methylbenzenesulfonic acid (1:1) | 736288 | |
| 32 | $R^1$ = $R^3$ = $R^4$ = H, $R^2$ = —OCH$_3$, X = 4-CH$_3$C$_6$H$_4$SO$_3^-$<br>CAS # 749787-74-4 Iodonium, (4-methoxyphenyl)-2-thienyl-, salt with 4-methyl-benzenesulfonic acid (1:1) | 736320 | 6,7,8,9 |
| 33 | $R^1$ = $R^2$ = H, $R^3$ = I, $R^4$ = —C$_6$H$_5$, X = 4-CH$_3$C$_6$H$_4$SO$_3^-$<br>Iodonium, phenyl(5-iodo-4-phenyl-2-thienyl)-, salt with 4-methyl-benzenesulfonic acid (1:1) | 751507 | 22,23 |

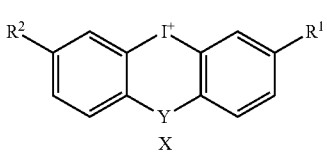

X

| | | | |
|---|---|---|---|
| 34 | $R^1$ = $R^2$ = —NO$_2$, Y = O, X = Cl$^-$<br>CAS # 96686-19-0 Pheniodoxin-5-ium, 3,7-dinitro-, chloride | 740103 | |
| 35 | $R^1$ = $R^2$ = —NH$_2$, Y = O, X = Cl$^-$<br>CAS # 96686-20-3 Pheniodoxin-5-ium, 3,7-diamino-, chloride | 740284 | 16 |
| 36 | $R^1$ = $R^2$ = —NO$_2$, Y = CH$_2$, X = Cl$^-$<br>CAS # 2582-62-9 10H-Dibenz[b,e]iodinium, 3,7-dinitro-, chloride | 740230 | 16 |
| 37 | $R^1$ = $R^2$ = —N(CH$_3$)$_2$, Y = CH$_2$, X = I$^-$<br>CAS # 194014-93-2 10H-Dibenz[b,e]iodinium, 3,7-bis(dimethylamino)-, iodide | 740541 | 14 |
| 38 | $R^1$ = $R^2$ = —N(CH$_3$)$_2$, Y = CH$_2$, X$^-$ = CH$_3$SO$_3^-$<br>10H-Dibenz[b,e]iodinium, 3,7-bis(dimethylamino)-, methanesulfonate<br>10H-Dibenz[b,e]iodinium, 3,7-bis(dimethylamino)-, iodide, dihydroiodide | 740542 | 14 |
| 39 | $R^1$ = $R^2$ = H, Y = —NCOCH$_3$, X = Br$^-$<br>CAS # 2582-68-5 10H-Pheniodazin-5-ium, 10-acetyl-, bromide | 740831 | 11,19,20 |

TABLE 1-continued

| Compound Description | | NSC Number | Ref.* |
|---|---|---|---|
| 40 | $R^1 = R^2 = H$, Y = —NCOCH$_3$, X = CH$_3$SO$_3^-$ CAS # 46782-31-4 10H-Pheniodazin-5-ium, 10-acetyl-, methanesulfonate | 741193 | 11,19,20 |

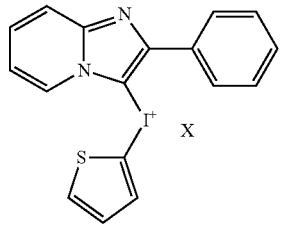

| | | | |
|---|---|---|---|
| 41 | X = I$^-$ [1,4]Iodoxino[2,3-f:6,5-f′]diquinolin-14-ium, iodide | 740830 | 17 |
| 42 | X = CH$_3$SO$_3^-$ [1,4]Iodoxino[2,3-f:6,5-f′]-diquinolin-14-ium, methane-sulfonate | 741003 | |

| | | | |
|---|---|---|---|
| 43 | $R^1$ = H, X = 4-CH$_3$C$_6$H$_4$SO$_3^-$ Iodonium, (2-phenylimidazo-[1,2-a]pyridin-3-yl)phenyl-, salt with 4-methylbenzenesulfonic acid (1:1) | 749821 | 6,7,21 |
| 44 | $R^1$ = F, X = 4-CH$_3$C$_6$H$_4$SO$_3^-$ Iodonium, [2-(4-fluorophenyl)-imidazo[1,2-a]pyridin-3-yl]phenyl-, salt with 4-methylbenzenesulfonic acid (1:1) | 750765 | 6,7,21 |

| | | | |
|---|---|---|---|
| 45 | $R^1$ = H, X = 4-CH$_3$C$_6$H$_4$SO$_3^-$ Iodonium, (2-hydroxy-4,4-di-methyl-6-oxo-1-cyclohexen-1-yl)-2-thienyl-, salt with 4-methyl-benzenesulfonic acid (1:1) | 743446 | |
| 46 | $R^1$ = —CO$_2$CH$_3$, X = 4-CH$_3$C$_6$H$_4$SO$_3^-$ Iodonium, (2-hydroxy-3-methoxy-carbonyl-4,4-dimethyl-6-oxo-1-carbonyl-4,4-dimethyl-6-oxo-1-salt with 4-methylbenzenesulfonic acid (1:1) | 743668 | |
| 47 | $R^1$ = -5(3-methylisoxazolyl), X = 4-CH$_3$C$_6$H$_4$SO$_3^-$ Iodonium, [2-hydroxy-3-(3-methyl-5-isoxazolyl)-4,4-dimethyl-6-oxo-1-cyclohexen-1-yl]-2-thienyl-, salt with 4-methylbenzenesulfonic acid (1:1 | 743861 | |

TABLE 1-continued

| | Compound Description | NSC Number | Ref.* |
|---|---|---|---|
| 48 | X = 4-CH₃C₆H₄SO₃⁻<br>Iodonium, (2-phenylimidazo-[1,2-a]pyridin-3-yl)thienyl-, salt with 4-methylbenzenesulfonic acid (1:1) | 750000 | |

*Reference for synthetic approach for making the iodonium analog compound

1. Cragoe, Edward J., Jr.; Woltersdorf, Otto W., Jr.; "(1-Oxo-2-aryl or thienyl-2-substituted-5-indanyloxy (or thio) alkanoic acids and derivatives"; U.S. Pat. No. 4,096,267 (1978).
2. Beringer, F. Marshall; Bachofner, H. Elizabeth; Falk, Robert A.; Leff, Milton; "Diaryliodonium Salts. VII. 2,2'-Dithienyl- and Phenyl-2-thienyliodonium Salts"; J. Am. Chem. Soc., 1958, 80, 4279.
3. Stang, Peter J.; Tykwinski, Rik; Zhdankin, Viktor V.; "Preparation of bis(Heteroaryl)iodonium Salts via an Iodonium Transfer Reaction Between Di(cyano)iodonium Triflate and Organostannes"; J. Heterocyclic Chern. 1992, 29, 815.
4. D'Auria, Maurizio; Esposito, Vittorio; Mauriello, Giacomo; "Photochemical Reactivity of Aromatic and Heteroaromatic Nitroderivatives in the Presence of Arylalkenes"; Tetrahedron 1996, 52, 14253.
5. Kazmierczak, Pawel; Skulski, Lech; "A Short-Cut Synthesis of Diaryliodonium Bromides Followed by Oxidative Anion Metatheses"; Synthesis 1995, 1027.
6. Togo, Hideo; Nabana, Takahiro; Yamaguchi, Kentaro; "Preparation and Reactivities of Novel (Diacetoxyiodo) arenes Bearing Heteroaromatics"; J. Org. Chern. 2000, 65, 8391.
7. Nabana, Takahiro; Togo, Hideo; "Reactivities of Novel [Hydroxy-(tosyloxy)iodo)arenes and [Hydroxy(phosphoryloxy)iodo)arenes for -Tosyloxylation and -Phosphoryloxylation of Ketones"; J. Org. Chern. 2002, 67, 4362.
8. Moriarity, Robert M.; Penmasta, Raju; Prakash, Indra; "Novel Penta-fluorophenyl Hypervalent Iodine Reagents"; Tetrahedron Lett. 1987, 877.
9. McKillop, Alexander; Kemp, Duncan; "Further Functional Group Oxidations Using Sodium Perborate"; Tetrahedron 1989, 45, 3299.
10. Wasylewsky, Alex; Brown, Robert K.; Sandin, Reuben B.; "Preparation of 4-Nitrodiphenyleneiodonium Chloride"; J. Am. Chem. Soc. 1950, 72, 1038.
11. Beringer, F. Marshall; Kravetz, Louis; Topliss, Geraldine B.; "Iodonium Salts Containing Heterocyclic Iodine"; J. Org. Chern. 1965, 30, 1141.
12. Blatchly, J. M.; McOmie, J. F. W.; Watts, M. L.; "Biphenylenes. Part VII. Synthesis of 2,3-Dimethoxybiphenylene"; J. Chern. Soc. 1962, 5085.
13. Huang, Wen-Kuei; Chang, C. C.; "Heterocyclic compounds containg iodine. IV. Synthesis of 3,6-dialkylaminodiphenyl heterocyclic compounds"; K'o Hsueh T'ung Pao 1963, 11, 47.
14. Hwang, Wen-Kuei; "Studies on Heterocyclic Compounds Containing Iodine. II. The Synthesis of 3,6-Di[Dimethylamino]dibenzo-pyriodonium Salts (III) and Their Properties"; Huaxue Xuebao 1957, 23, 438.
15. Ding, Zhaozhong; Hou, Zigie; Huang, Wenkui; "Improved Synthesis of 3,6-Diaminobiphenyl Fused Iodine-Containing Heterocycles"; Lanzhou Daxue Xuebao, Ziran Kexueban 1984, 20 (1), 169.
16. Hou, Zijie; Huang, Wenkui; Synthesis of 3,6-Dihalodibenzo-cycloiodonium Salts" Lanzhou Daxue Xuebao, Ziran Kexueban 1984, (4), 67.
17. Zhang, Gongchen; Tan, Zhen; Li, Yulin; "Synthesis of the 8-oxadiquino [5,6-b;6',5'-e]pyriodonium compound"; Yingyong Huaxue 1986, 1(4), 48.
18. Hwang, Wen-Kuei; "Studies on Heterocyclic Compounds Containing Iodine. I. The Preparation of 3,6-Dinitrodibenzopyriodonium Salts (III) and Their Properties"; Sci. Sin. (Engl. Ed.) 1957, 6, 123.
19. Kehrmann, F.; Baumgartner, E.; "Uber Acetylierung von Derivaten des Diphenylamins mit Essigsaure-anhydrid and Zinkchloid"; Helv. Chim. Acta. 1926, 2, 673.
20. Smith, Peter A S.; Brown, Bernard Beau; Putney, Richard K.; Reinisch, Ronald F.; "The Synthesis of Heterocyclic Compounds from Aryl Azides. III. Some Six-membered Rings and Some Azidobiaryls"; J. Am. Chem. Soc. 1953, 75, 6335.
21. Cëcile Enguehard, Jean-Louis Renou, Valérie Collot, Maud Hervet, Sylvain Rault, and Alain Gueiffier; "Reactivity of 3-Iodoimidazo[1,2-a]pyridines Using a Suzuki-Type Cross-Coupling Reaction"; J. Org. Chem., 2000, 65, 6572.
22. Alexander L. Johnson; "Synthesis of the Three Isomeric Ortho-Substituted Phenylthienyl Benzoic Acids"; J. Org. Chem., 1976, 41, 1320.
23. Richard M. Kellogg, A. Paul Schaap, Edwin T. Harper, Hans Wynbert; "Acid-Catalyzed Brominations, Deuterations, Rearrangements, and Debrominations of Thiophenes under Mild Conditions"; J. Org. Chem., 1968, 33, 2902.

Compound 4 Iodonium, Di-2-Thienyl-, Salt with Methanesulfonic Acid (1:1)

To a solution of iodonium, di-2-thienyl-, chloride (682 mg, 1.92 mmol) in deionized water (30.0 mL) at 60° C. was added a hot solution of silver methanesulfonate (390 mg, 1.92 mmol) in deionized water (2.00 mL). The hot suspension was stirred for 10 minutes, then gravity filtered to remove AgCl. The filtrate was concentrated to dryness, and the residue was coevaporated with CH3CN (2×5 mL). The crude solid was dissolved in warm CH3CN (20 mL) and then CH2Cl2 (5 mL) was slowly added, followed by the dropwise addition of Et2O (5 mL). The suspension was concentrated to dryness and the residue was triturated with a mixture of CH3CN/Et2O (3 mL/10 mL). The suspension was suction filtered and the filter cake was washed with Et2O (20 mL). The solid was dried in vacuo at room temperature to give pure compound 4 (515 mg, 69%); m.p. 117-121° C. (dec)(uncorrected).

Nuclear Magnetic Resonance Spectroscopy:
$^1$H NMR (500 MHz, DMSO-d6): δ 8.05-8.04 (d, 2H); 7.96-7.94 (d, 2H); 7.17-7.15 (m, 2H); 2.29 (s, 3H).

Mass Spectroscopy: Method of Ionization: Electrospray (+ve) Calc'd for (C8H6IS2)+=293 Found: m/z (relative intensity) 293 (100%).

Compound 5 Iodonium, Di-2-Thienyl-, Salt with with Ethanesulfonic Acid (1:1)

Silver Ethanesulfonate

To a solution of silver nitrate (13.7 g, 80.6 mmol) in deionized water (25.0 mL) was added a solution of sodium hydroxide (3.30 g, 80.8 mmol) in deionized water (100 mL). The precipitated silver oxide was collected by suction filtration and washed with deionized water until the washes were ~pH 7. The silver oxide was used "as is" without further purification. To a cold (5-10° C.), stirring suspension of silver oxide (7.48 g, 32.3 mmol) in deionized water (8.00 mL) was added ethanesulfonic acid (7.18 g, 65.2 mmol). The mixture was stirred until a clear solution was obtained (15-30 minutes), and then suction filtered. The filtrate was concentrated to dryness and the residue was suspended in acetone (50 mL). The suspension was suction filtered and the filter cake was washed with acetone (200 mL), then dried in vacuo at room temperature to give silver ethanesulfonate (4.5 g, 64%).

To a solution of iodonium, di-2-thienyl-, chloride (750 mg, 2.28 mmol) in deionized water (30.0 mL) at 75° C. was added a hot solution of silver ethanesulfonate (495 mg, 2.28 mmol) in deionized water (1.5 mL). The hot suspension was stirred for 5 minutes, then gravity filtered to remove AgCl. The filtrate was concentrated to dryness, and the residue was coevaporated with CH3CN (3×30 mL) and Et2O (30 mL). The crude solid was dissolved in warm CH3CN (4.5 mL) and then CH2Cl2 (7.5 mL) was slowly added, followed by the dropwise addition of Et2O (17 mL). The suspension was suction filtered, washed with Et2O (3×10 mL), and dried in vacuo at room temperature to give crude 4 (511 mg, 56%). The solid was dissolved in warm CH3CN (3.6 mL) and then CH2Cl2 (6.0 mL) was slowly added, followed by the dropwise addition of Et2O (6.0 mL). The suspension was diluted with additional Et2O (7.0 mL) and suction filtered. The filter cake was washed with Et2O (2×5 mL) and dried in vacuo at room temperature to give pure compound 5 (384 mg, 42%); m.p. 104-107° C. (dec)(uncorrected).

Nuclear Magnetic Resonance Spectroscopy:

$^1$H NMR (500 MHz, DMSO-d6): δ 8.05-8.04 (dd, 2H); 7.96-7.94 (dd, 2H); 7.17-7.15 (dd, 2H); 2.37-2.33 (q, 2H); 1.06-1.03 (t, 3H).

Mass Spectroscopy:

Method of Ionization: Electrospray (+ve) Calc'd for (C8H6IS2)+=293 Found: m/z (relative intensity) 293 (100%).

Compound 6 Iodonium, (5-Nitro-2-Thienyl)-2-Thienyl-, Salt with Methane-Sulfonic Acid (1:1)

Thiophene, 2-iodo-5-nitro-

To cold (−20° C.), stirring acetic anhydride (13.4 mL, 142 mmol) was slowly added dropwise, with stirring, fuming nitric acid (3.20 mL, 68.1 mmol), maintaining the internal temperature between −10 and −20° C. When the addition was completed, a solution of 2-nitrothiophene (7.00 g, 33.3 mmol) in acetic anhydride (6.00 mL) was slowly added dropwise, maintaining the internal temperature between −10° C. and −20° C. The reaction mixture was stirred at −10 to −15° C. for 0.5 hour, then poured into a mixture of ice (25 g) and water (100 mL). After standing at room temperature for 1.0 hour, the suspension was suction filtered and the solid was washed with water (200 mL). The crude solid was dissolved in EtOH (20 mL) and chilled at −20° C. for 20 hours. The solid was collected by suction filtration and dried in vacuo to give thiophene, 2-iodo-5-nitro- (4.3 g, 51%).

Iodonium, (5-nitro-2-thenyl)-2-thienyl-, Bromide

Chromium (VI) oxide (1.10 g, 11.0 mmol) was dissolved in a cooled (5-10° C.) mixture of HOAc (7.50 mL) and Ac2O (3.5 mL). To the cold solution was added thiophene, 2-iodo-5-nitro- (3.825 g, 15.0 mmol), followed by the slow, dropwise addition of conc. H2SO4 (2.50 mL, 45.0 mmol), maintaining the internal temperature below 10° C. When the addition was completed, the mixture was stirred at room temperature for 90 minutes. The mixture was cooled to 5-10° C. and thiophene (1.157 g, 13.75 mmol) was added dropwise, maintaining the internal temperature below 10° C. When the addition was completed, the mixture was stirred at room temperature for 20 minutes, then poured into hot water (30 mL) and stirred at room temperature for 1.0 hour. The mixture was filtered and the green-colored filtrate was cooled to 10-15° C. and a solution of KBr (2.4 g) in water (11 mL) was added dropwise. The resulting suspension was stirred at room temperature for 30 minutes and then suction filtered. The solid was washed with water (600 mL) and acetone (100 mL), then dried in vacuo at room temperature to give iodonium, (5-nitro-2-thenyl)-2-thienyl-, bromide (950 mg, 15%). Iodonium, (5-nitro-2-thenyl)-2-thienyl-, salt with methanesulfonic acid (1:1)

To a solution of iodonium, (5-nitro-2-thenyl)-2-thienyl-, bromide (250 mg, 0.598 mmol) in deionized water (125 mL) at 90° C. was added a hot solution of silver methanesulfonate (121 mg, 0.596 mmol) in deionized water (2.00 mL). The hot suspension was gravity filtered to remove AgCl. The filtrate was concentrated to dryness, and the residue was coevaporated with CH3CN (2×5 mL). The crude solid was dissolved in CH2Cl2 (10 mL) and then slowly added to stirring Et2O (150 mL). The suspension was stirred at room temperature for 0.5 hour. The solvent was decanted off and the residue was triturated with Et2O (50 mL). The solvent was decanted off and the solid was dried in vacuo to give pure iodonium, (5-nitro-2-thienyl)-2-thienyl-, salt with methanesulfonic acid (1:1) compound 6 (185 mg, 71%); m.p. 119-121° C. (dec)(uncorrected).

Nuclear Magnetic Resonance Spectroscopy:

$^1$H NMR (400 MHz, DMSO-d6): δ 8.19-8.18 (d, 1H); 8.10-8.09 (d, 1H); 8.06-7.97 (m, 2H); 7.25-7.24 (d, 1H); 2.31 (s, 3H).

Mass Spectroscopy:

Method of Ionization: Electrospray (+ve) Calc'd for (C8H5INO2S2)+=338 Found: m/z (relative intensity) 338 (60%).

Compound 7 Iodonium, [5-[2-(dimethylamino)-2-oxoethyl]-2-thienyl]-2-thienyl-, Salt with 4-methyl-benzenesulfonic Acid (1:1)

2-(Diacetoxyiodo)thiophene

To a stirring solution of 2-iodothiophene (8.40 g, 40.0 mmol) in glacial acetic acid (400 mL) at 40° C. under an argon atmosphere, was added sodium perborate tetrahydrate (61.6 g, 400 mmol), portion wise over 0.5 h. After the addition was completed, the reaction mixture was stirred and heated at 40° C. for 4 h. Cooled to 25-30° C. and concentrated the mixture to dryness. Partitioned the residue between water (200 mL) and CH2Cl2 (200 mL). The water layer was extracted with CH2Cl2 (3×100 mL), and the combined organic layer was dried (Na2SO4) and concentrated to give a thick slurry. The slurry was diluted with CH2Cl2 (20 mL) and hexanes (200 mL) and then suction filtered. The solid was washed with hexanes (3×25 mL) and dried in vacuo at room temperature to give 2-(Diacetoxyiodo)thiophene (4.1 g, 31%).

2-[Hydroxy(tosyloxy)iodo]thiophene

To a solution of 2-(Diacetoxyiodo)thiophene (820 mg, 2.50 mmol) in CH3CN (25.0 ml) at room temperature under argon, was added toluenesulfonic acid monohydrate (950 mg, 5.00 mmol). The resulting bright yellow solution yielded a white precipitate within a few minutes. The mixture was stirred at room temperature for 15 minutes and then suction filtered. The solid was washed with Et2O (25 mL) and rapidly sucked dry to give 2-[Hydroxy(tosyloxy) iodo]thiophene (870 mg, 87%). This material is unstable at room temperature and was used immediately in the next step.

Thiophene, [2-(dimethylamino)-2-oxoethyl]-

Dichloromethane (30 mL) was saturated with dimethylamine gas at 5° C. and then a solution of 2-thiopheneacetyl chloride (1 mL, 8.11 mmol) in dichloromethane (20 mL) was added dropwise. When the addition was completed, the reaction mixture was stirred at room temperature for 1 hour. The reaction mixture was poured into Et2O (400 mL) and the resulting precipitate (dimethylamine hydrochloride) was removed by filtration. The filtrate was concentrated to dryness and then dissolved in Et2O (20 mL) and diluted with hexanes (20 mL). The clear solution (no more dimethylamine hydrochloride had precipitated) was concentrated to dryness to give Thiophene, [2-(dimethylamino)-2-oxoethyl]- (0.79 g, 58%), as a tan-colored liquid.

Iodonium, [5-[2-(dimethylamino)-2-oxoethyl]-2-thienyl]-2-thienyl-, Salt with 4-methylbenzenesulfonic Acid (1:1)

To a stirring solution of 2-[Hydroxy(tosyloxy)iodo]thiophene (870 mg, 2.185 mmol) in glacial acetic acid (15 mL)(warmed to give a solution then cooled back to room temperature) was added a solution of Thiophene, [2-(dimethylamino)-2-oxoethyl]- (366 mg, 2.163 mmol) in glacial acetic acid (2.5 mL). The reaction mixture was stirred at room temperature for 30 minutes. The dark green solution was added to stirring Et2O (1 L) to give a precipitate. The suspension was suction filtered and the solid was washed with Et2O (200 mL). The solid was dried in vacuo to give Iodonium, [5-[2-(dimethylamino)-2-oxoethyl]-2-thienyl]-2-thienyl-, salt with 4-methylbenzenesulfonic acid (1:1) (677 mg, 57%); m.p. 121-126° C. (dec)(uncorrected).

Nuclear Magnetic Resonance Spectroscopy:

$^1$H NMR (500 MHz, DMSO-d6): δ 8.03-8.02 (d, 1H); 7.95-7.94 (d, 1H); 7.88-7.87 (d, 1H); 7.48-7.46 (d, 2H); 7.16-7.14 (dd, 1H); 7.11-7.09 (d, 2H); 6.96-6.95 (d, 1H); 4.16 (s, 2H); 3.02 (s, 3H); 2.85 (s, 3H); 2.29 (s, 3H).

Mass Spectroscopy: Method of Ionization: Electrospray (+ve) Calc'd for (C12H13INOS2)+=378 Found: m/z (relative intensity) 378 (90%).

Compound 8 Iodonium, (5-iodo-2-thienyl)-2-thienyl-, salt with 4-methyl-benzenesulfonic Acid (1:1)

2-(Diacetoxyiodo)thiophene and 2-[Hydroxy(tosyloxy) iodo]thiophene were prepared according to the same process as described for Compound 7.

Iodonium, (5-iodo-2-thienyl)-2-thienyl-, Salt with 4-methylbenzenesulfonic Acid (1:1)

To a stirring solution of 2-[Hydroxy(tosyloxy)iodo]thiophene (850 mg, 2.135 mmol) in glacial acetic acid (15 mL)(warmed to give a solution then cooled back to room temperature) was added a solution of 2-iodothiophene (449 mg, 2.23 mmol) in glacial acetic acid (2.5 mL). The reaction mixture was stirred at room temperature for 30 minutes. The amber-colored solution was added to stirring Et2O (1 L) to give a precipitate. The suspension was suction filtered and the solid was washed with Et2O (200 mL). The solid was dried in vacuo to give Iodonium, (5-iodo-2-thienyl)-2-thienyl-, salt with 4-methylbenzenesulfonic acid (1:1) (892 mg, 71%); m.p. 123-127° C. (dec)(uncorrected).

Nuclear Magnetic Resonance Spectroscopy:

$^1$H NMR (500 MHz, DMSO-d6): δ 8.06-8.05 (dd, 1H); 7.97-7.96 (dd, 1H); 7.72-7.71 (d, 1H); 7.48-7.46 (d, 2H); 7.43-7.42 (d, 1H); 7.18-7.17 (dd, 1H); 7.11-7.10 (d, 2H); 2.28 (s, 3H).

Mass Spectroscopy:

Method of Ionization: Electrospray (+ve) Calc'd for (C8H5I2S2)+=418.8 Found: m/z (relative intensity) 418.8 (100%).

Compound 9 Iodonium, [5-(hydroxymethyl)-2-thienyl]-2-thienyl-, Salt with 4-methylbenzenesulfonic Acid (1:1)

2-(Diacetoxyiodo)thiophene and 2-[Hydroxy(tosyloxy) iodo]thiophene were prepared according to the same process as described for Compound 7.

Iodonium, [5-(hydroxymethyl)-2-thienyl]-2-thienyl-, Salt with 4-methylbenzenesulfonic Acid (1:1)

To a stirring solution of 2-[Hydroxy(tosyloxy)iodo]thiophene (849 mg, 2.13 mmol) in glacial acetic acid (15 mL)(warmed to give a solution then cooled back to room temperature) was added a solution of thiophen-2-ylmethanol (245 mg, 2.14 mmol) in glacial acetic acid (2.5 mL). The reaction mixture was stirred at room temperature for 30 minutes. The green solution was added to stirring Et2O (1 L) to give a milky suspension. The suspension was suction filtered and the oily residue was dissolved in EtOH (10 mL) and then added dropwise to stirring Et2O (500 mL). The resulting milky white suspension was allowed to stand at room temperature for 1.5 hours. The precipitated white solid was isolated by centrifugation. The solid was washed with Et2O (3×20 mL) by centrifugation and then the centrifuge tube containing the solid was capped with a rubber septum. An argon line with needle was introduced through the septum along with a vent needle. The argon flow was started and continued until the solid was dry. At this time the solid was dried in vacuo at room temperature to give iodonium, [5-(hydroxymethyl)-2-thienyl]-2-thienyl-, salt with 4-methylbenzenesulfonic acid (1:1)

(384 mg, 36%); m.p. 122-125° C. (dec)(uncorrected).

Nuclear Magnetic Resonance Spectroscopy:

$^1$H NMR (500 MHz, DMSO-d6): δ 8.04-8.03 (dd, 1H); 7.95-7.94 (dd, 1H); 7.91-7.90 (d, 1H); 7.48-7.46 (d, 2H); 7.17-7.15 (dd, 1H); 7.11-7.10 (d, 2H); 6.97-6.96 (d, 1H); 5.80-5.77 (t, 1H); 4.74-4.72 (d, 2H); 2.29 (s, 3H).

Mass Spectroscopy:

Method of Ionization: Electrospray (positive ion) Calc'd for (C9H8IOS2)+=322.9 Found: m/z (relative intensity) 322.9 (100%).

Compound 10 Iodonium, [5-[2-(acetylamino)-ethyl]-2-thienyl]-2-thienyl-, Salt with 4-methylbenzene-sulfonic Acid (1:1)

2-(Diacetoxyiodo)thiophene and 2-[Hydroxy(tosyloxy)iodo]thiophene were prepared according to the same process as described for Compound 7.

Thiophene, 2-(acetylamino)ethyl-

To a stirring solution of 2-(thiophen-2-yl)ethanamine (1.1 g, 8.3 mmol) in pyridine (20 mL) was added acetic anhydride (3.0 mL, 31.7 mmol) dropwise. When the addition was completed, the reaction mixture was stirred at room temperature for 24 hours. The reaction mixture was diluted with EtOAc (100 mL) and then washed with 1 N HCl(aq)(3×50 mL) and brine (3×50 mL). The organic layer was dried (Na2SO4), filtered and concentrated to give an oil. The oil was coevaporated with CH2Cl2/hexanes (20 mL/10 mL) and Et2O (25 mL) to give Thiophene, 2-(acetylamino)ethyl-(660 mg, 47%), as a tan solid.

Iodonium, [5-[2-(acetylamino)ethyl]-2-thienyl]-2-thienyl-, salt with 4-methylbenzenesulfonic acid (1:1)

To a stirring suspension of 2-[Hydroxy(tosyloxy)iodo]thiophene (860 mg, 2.16 mmol) in CHCl3 (45 mL) was added a solution of Thiophene, 2-(acetylamino)ethyl-(366 mg, 2.16 mmol) in CHCl3 (5 mL). To this stirring suspension was added glacial acetic acid (5 mL) and the reaction mixture was stirred at room temperature for 40 minutes (clear yellow solution). This yellow solution was added to cold (5-10° C.), stirring Et2O (800 mL) to give a precipitate. The suspension was stored at −20° C. for 2 hours and then the solid was isolated by centrifugation. The solid was washed with Et2O (5×20 mL) by centrifugation. The solid is hygroscopic. The target compound Iodonium, [5-[2-(acetylamino)ethyl]-2-thienyl]-2-thienyl-, salt with 4-methylbenzenesulfonic acid (1:1) was estimated to be 90% purity as shown by the 1H NMR.

Nuclear Magnetic Resonance Spectroscopy:

$^1$H NMR (500 MHz, DMSO-d6): δ 8.03-8.02 (m, 1H); 7.98-7.94 (m, 2H); 7.89-7.88 (d, 1H); 7.49-7.47 (d, 2H); 7.16-7.15 (dd, 1H); 7.11-7.10 (d, 2H); 6.95-6.94 (d, 1H); 3.29-3.25 (dd, 2H); 3.04-3.01 (t, 2H); 2.29 (s, 3H); 1.77 (s, 3H).

Mass Spectroscopy:

Method of Ionization: Electrospray (positive ion) Calc'd for (C12H13INOS2)+=378 Found: m/z (relative intensity) 378 (100%).

Compound 11 Iodonium, [5-(2-formyl-6-pyridinyl)-2-thienyl]-2-thienyl-, Salt with 4-methylbenzenesulfonic Acid (1:1)

2-(Diacetoxyiodo)thiophene and 2-[Hydroxy(tosyloxy)iodo]thiophene were prepared according to the same process as described for Compound 7.

Iodonium, [5-(2-formyl-6-pyridinyl)-2-thienyl]-2-thienyl-, Salt with 4-methylbenzenesulfonic Acid (1:1)

To a stirring solution of 2-[Hydroxy(tosyloxy)iodo]thiophene (901 mg, 2.26 mmol) in glacial acetic acid (15 mL)(warmed to give a solution then cooled back to room temperature) was added a solution of 6-(thiophen-2-yl)picolinaldehyde (428 mg, 2.26 mmol) in glacial acetic acid (2.5 mL). The reaction mixture was stirred at room temperature for 30 minutes. The yellow milky suspension was added to stirring Et2O (1 L) to give a precipitated solid. The suspension was suction filtered and the solid was washed with Et2O (125 mL). The solid was dried in vacuo at room temperature to give Iodonium, [5-(2-formyl-6-pyridinyl)-2-thienyl]-2-thienyl-, salt with 4-methylbenzenesulfonic acid (1:1) (632 mg, 44%); m.p. 168-171° C. (dec)(uncorrected) as an approximately 92:8 mixture of desired product to compound 8, as shown by the elemental analysis and mass spectrum results.

Nuclear Magnetic Resonance Spectroscopy:

$^1$H NMR (500 MHz, DMSO-d6): δ 9.96 (s, 1H); 8.30-8.28 (dd, 1H); 8.18-8.15 (t, 1H); 8.12-8.11 (dd, 2H); 7.98-7.97 (dd, 1H); 7.94-7.93 (d, 1H); 7.90-7.89 (dd, 1H); 7.48-7.46 (d, 2H); 7.19-7.18 (dd, 1H); 7.11-7.09 (d, 2H); 2.28 (s, 3H).

Mass Spectroscopy: Method of Ionization: Electrospray (positive ion) Calc'd for (C14H9INOS2)+=397.9 Found: m/z (relative intensity) 397.9 (100%); 418.7 (8%, cation of compound 8).

Compound 12 Iodonium, [5-[[(9-fluorenyl-methoxycarbonyl)amino]methyl]-2-thienyl]-2-thienyl-, Salt with p-toluenesulfonic Acid (1:1)

2-(Diacetoxyiodo)thiophene and 2-[Hydroxy(tosyloxy)iodo]thiophene were prepared according to the same process as described for Compound 7.

Thiophene, 2-[[(9-fluorenylmethoxycarbonyl)amino]methyl]-

To a stirring solution of 9-fluorenylmethyl chloroformate (4.00 g, 15.46 mmol) in Et2O (200 mL) was slowly added a solution of thiophene-2-methylamine (3.51 g, 31.01 mmol) in Et2O (100 mL). When the addition was completed, Et2O (60 mL) was added to the slurry and stirring was continued for at room temperature for 45 minutes. The suspension was suction filtered and the solid was washed with Et2O (3×15 mL). The combined filtrate and washings was washed with water (3×150 mL), dried (Na2SO4), and concentrated to give a white solid. The solid was dried in vacuo to give thiophene, 2-[[(9-fluorenylmethoxycarbonyl)amino]methyl]- (4.5 g, 87%).

Iodonium, [5-[[(9-fluorenylmethoxycarbonyl)amino]methyl]-2-thienyl]-2-thienyl-, Salt with p-toluenesulfonic Acid (1:1)

To a stirring solution of 2-[hydroxy(tosyloxy)iodo]thiophene (1.90 g, 4.77 mmol) in glacial acetic acid (39.0 mL)(warmed to give a solution then cooled back to room temperature) was added thiophene, 2-[[(9-fluorenyl-methoxycarbonyl)amino]methyl]- (1.60 g, 4.77 mmol). Warmed the reaction mixture to give a solution then cooled back to room temperature and stirred at room temperature for 30 minutes. The green solution was added to stirring Et2O (650 mL) to give a precipitate. The milky solution was decanted off and the solid was washed with Et2O (100 mL). The solid was suspended in Et2O (25 mL) and collected by suction filtration to give a first crop of iodonium, [5-[[(9-fluorenylmethoxycarbonyl)amino]methyl]-2-thienyl]-2-thienyl-, salt with p-toluenesulfonic acid (1:1) (1.2 g). The milky solution was further diluted with Et2O (150 mL) and chilled at 0-5° C. for 1.0 h. The resulting suspension was suction filtered and the solid was washed with Et2O (50 mL) and dried in vacuo to give a second crop (585 mg). Total yield of 52%; m.p. 85-88° C. (uncorrected).

Nuclear Magnetic Resonance Spectroscopy:
1H NMR (500 MHz, DMSO-d6): δ 8.12-8.09 (t, 1H); 8.06-8.05 (d, 1H); 7.96-7.95 (d, 1H); 7.92-7.90 (m, 3H); 7.68-7.67 (d, 2H); 7.49-7.47 (d, 2H); 7.45-7.42 (t, 2H); 7.34-7.31 (t, 2H); 7.17-7.15 (t, 1H); 7.12-7.11 (d, 2H); 6.96-6.95 (d, 1H); 4.43-4.42 (d, 2H); 4.38-4.36 (d, 2H); 4.24-4.21 (t, 1H); 2.30 (s, 3H).

Mass Spectroscopy:
Method of Ionization: Electrospray (+ve) Calc'd for (C24H19INO2S2)+=544 Found: m/z (relative intensity) 544 (100%).

Compound 14 CAS no. 46502-38-9
Dibenz[b,d]iodolium, 3-nitro-, Chloride

Dibenz[b,d]iodolium Tosylate

To a vigorously stirred solution of 2-iodobiphenyl (24.0 g, 85.7 mmol) in acetonitrile (210 mL) at room temperature was added [hydroxy(tosyloxy)iodo]benzene (33.6 g, 85.7 mmol). The reaction mixture was stirred at room temperature for 4 days. The reaction mixture was suction filtered and the filter cake was washed with Et2O (400 mL). The solid was dried in vacuo at room temperature to give Dibenz[b,d]iodolium tosylate (34.8 g, 90%).

Dibenz[b,d]iodolium Chloride

To a solution of Dibenz[b,d]iodolium tosylate (17.1 g, 38.0 mmol) in formic acid (88%, 590 mL) at 75° C. was added a solution of potassium chloride (34.2 g, 459 mmol) in water (177 mL). A thick, white precipitate formed immediately. The reaction mixture was suction filtered while still warm and the solid was washed with water (200 mL) and EtOAc (200 mL), then dried in vacuo at room temperature to give Dibenz[b,d]iodolium chloride (10.0 g, 84%).

Dibenz[b,d]iodolium Nitrate

To a vigorously stirred suspension of Dibenz[b,d]iodolium chloride (15.0 g, 47.7 mmol) in deionized water (666 mL) at 95° C. was added a solution of silver nitrate (16.7 g, 98.3 mmol) in hot deionized water (10 mL). The reaction mixture was treated with a solution of sodium nitrate (222 g, 2610 mmol) in hot deionized water (260 mL), and stirring was continued at 95 C for 0.5 hour. The reaction mixture was cooled to 5-10 C (ice water bath) and suction filtered through shark skin. The filter cake was suspended in deionized water (2.67 L) and then stirred and heated at 95 C for 0.5 hour (intermediate 3 is soluble in hot water). The hot reaction mixture was suction filtered through shark skin to remove silver chloride, and the hot filtrate (clear and colorless) was treated with sodium nitrate (129 g). Intermediate Dibenz[b,d]iodolium nitrate immediately precipitated from solution and was collected by suction filtration (shark skin). The solid was dried in vacuo at 45-50 C to give Dibenz[b,d]iodolium nitrate (15.6 g, 96%).

Dibenz[b,d]iodolium, 3-nitro-, Sulfate (2:1)

Dibenz[b,d]iodolium nitrate (10.0 g, 29.3 mmol) was slowly added portionwise to cold (5-10 C), stirring concentrated sulfuric acid (30.0 mL) over 15 minutes. When the addition was completed, the reaction mixture was allowed to stand at room temperature for 0.5 hour (Note 2). The reaction mixture (pale yellow solution) was added to crushed ice (400 g), and the precipitated solid was collected by suction filtration (shark skin). The filter cake was washed with water (2 L), EtOH (2×300 mL), and Et2O (2×300 mL). The solid was dried in vacuo at 40-50 C to give crude 4. The 1H NMR spectrum showed that this material was contaminated with ~10% of an isomeric material. The solid was triturated in boiling water (800 mL) for 1.5 hours. The hot suspension was suction filtered, and the filter cake was washed with hot water (400 mL). The solid was suspended in EtOH (300 mL) and suction filtered. The filter cake was washed with EtOH (2×50 mL) and Et2O (3×50 mL). The solid was dried in vacuo at 40-50° C. to give Dibenz[b,d]iodolium, 3-nitro-, sulfate (2:1) (8.1 g, 74%). The 1H NMR showed that there was still impurity present. The solid was triturated in boiling water (1 L) for 2 hours, then suction filtered hot and washed with hot water (3×50 mL), EtOH (3×10 mL) and Et2O (3×25 mL). The solid was dried in vacuo at 40-50 C to give pure product (6.52 g, 60%).

Dibenz[b,d]iodolium, 3-nitro-, Nitrate

To a stirring suspension of Dibenz[b,d]iodolium, 3-nitro-, sulfate (2:1) (8.50 g, 22.8 mmol) in deionized water (550 mL) at 95-100° C. was added a solution of barium nitrate (6.09 g, 23.3 mmol) in hot deionized water (75.0 mL). The mixture was stirred at 90-95 C for 15 minutes, then cooled to 10° C. and suction filtered (shark skin). The filter cake was suspended in deionized water (1.70 L) and heated to 95-100 C to dissolve intermediate 5. The hot reaction mixture was gravity filtered to remove barium sulfate. To the clear, light yellow filtrate was added sodium nitrate (10.9 g). The resulting thick suspension was suction filtered (shark skin) and the filter cake was washed with deionized water (100 mL). The solid was dried in vacuo at 45-50 C to give Dibenz[b,d]iodolium, 3-nitro-, nitrate (5.7 g, 65%).

Dibenz[b,d]iodolium, 3-nitro-, Chloride

A suspension of Dibenz[b,d]iodolium, 3-nitro-, nitrate (4.70 g, 12.2 mmol) in deionized water (1.71 L) was heated at 95 C for 0.5 hour to give a clear, light yellow solution. The heating source was removed and the hot solution was treated with hydrochloric acid (1.0 N, 103 mL) to give an immediate precipitation of target compound Dibenz[b,d]iodolium, 3-nitro-, chloride. The suspension was chilled in an icewater bath and then suction filtered through shark skin. The filter cake was washed with water until the filtrate was pH 5-6. The solid was dried in vacuo at 40-50 C to give Dibenz[b,d]iodolium, 3-nitro-, chloride (4.1 g, 94%); m.p. 282-285 C (dec, uncorrected).

Nuclear Magnetic Resonance Spectroscopy:
$^1$H NMR (500 MHz, DMSO-d6): δ 9.39-9.38 (d, 1H); 8.68-8.65 (m, 2H); 8.59-8.58 (d, 2H); 7.90-7.87 (t, 1H); 7.81-7.77 (t, 1H).

Compound 15 CAS #46980-64-7 Dibenziodolium, 3,7-dinitro-, Bromide

Dibenziodolium, 3,7-dinitro-, Hydrogensulfate

A solution of iodine (385 mg, 1.52 mmol) and potassium iodate (1.00 g, 4.67 mmol) in concentrated sulfuric acid (4.0 mL) was stirred at room temperature for 6 hours to give a yellow suspension of iodyl sulfate. The mixture was cooled to 5 C and 4,4'-dinitrobiphenyl (1.856 g, 7.60 mmol) was added. The reaction mixture was warmed to room temperature and then stirred at room temperature for 20 hours. The thick, yellow suspension was poured onto a mix of ice (25 g) and water (25 mL) to give a purple-colored suspension. The suspension was suction filtered and the solid was washed with water (5×25 mL). The solid was triturated in water (100 mL), hot water (200 mL), and EtOAc (200 mL), then dried in vacuo at room temperature to give Dibenziodolium, 3,7-dinitro-, hydrogensulfate (2.14 g, 60%).

Dibenziodolium, 3,7-dinitro-, bromide

To a hot, milky suspension of Dibenziodolium, 3,7-dinitro-, hydrogensulfate (260 mg, 0.558 mmol) in formic acid (88%, 20 mL) was added a solution of potassium bromide (200 mg, 1.68 mmol) in water (4.0 mL). The yellow-colored mixture immediately became a bright white color with precipitation of the bromide salt. The solid was collected by suction filtration, washed with water (3×20 mL) and EtOAc (3×20 mL), then dried in vacuo at 40-50 C to give Dibenziodolium, 3,7-dinitro-, bromide (240 mg, 96%).
Nuclear Magnetic Resonance Spectroscopy:
$^1$H NMR (400 MHz, DMSO-d6): δ 9.41-9.40 (d, 2H); 8.78-8.76 (d, 2H); 8.65-8.62 (dd, 2H).
Mass Spectroscopy:
Method of Ionization: Electrospray (+ve) Calc'd for (C12H6IN2O4)+=369 Found: m/z (relative intensity) 369 (35%).

Compound 16 CAS #96686-21-4 Dibenziodolium, 3,7-dibromo-, Bromide

Dibenziodolium, 3,7-diamino-, chloride synthesis is described for compound 18 below.

Dibenziodolium, 3,7-dibromo-, Bromide

To a cold (0-5 C), stirring suspension of Dibenziodolium, 3,7-diamino-, chloride (344 mg, 1.00 mmol) in 48% (aq) HBr (20 mL), was added dropwise a cold solution of sodium nitrite (160 mg, 2.32 mmol) in water (10 mL). When the addition was completed, stirred at 0 C for 1.5 hours. The bright yellow suspension was poured into a stirring solution of CuBr (1.0 g, 6.96 mmol) in 48% HBr (10.0 mL). The mix was stirred at room temperature for 4 hours then let stand at room temperature for 20 hours. The suspension was suction filtered and the solid was washed with water (4×25 mL) and acetone (3×10 mL), then dried in vacuo at 30 C to give 4 (407 mg, 79%); m.p. 202-205° C. (dec)(uncorrected)(lit. m.p. 216-218° C.).

Nuclear Magnetic Resonance Spectroscopy:
$^1$H NMR (500 MHz, DMSO-d6): δ 8.69 (d, 2H); 8.37-8.36 (d, 2H); 8.03-8.01 (dd, 2H).
Mass Spectroscopy:
Method of Ionization: Electrospray (+ve) Calc'd for (C12H6Br2I)+=434.9 Found: m/z (relative intensity) 434.9 (50%); 436.9 (100%); 438.9 (45%).

Compound 18 Dibenziodolium, 3,7-diamino-, Methanesulfonate

Dibenziodolium, 3,7-dinitro-, Hydrogensulfate

A solution of iodine (1.50 g, 5.91 mmol) and potassium iodate (3.86 g, 18.0 mmol) in concentrated sulfuric acid (14.0 mL) was stirred at room temperature for 6 hours to give a yellow suspension of iodyl sulfate. The mixture was cooled to 5° C. and 4,4'-dinitrobiphenyl (6.30 g, 29.4 mmol) was added. The reaction mixture was warmed to room temperature and then stirred at room temperature for 20 hours. The thick, yellow suspension was poured onto a mix of ice (55 g) and water (55 mL) to give a purple-colored suspension. The suspension was suction filtered and the solid was washed with water (3×50 mL). The solid was triturated in water (300 mL), hot water (500 mL), and EtOAc (3×300 mL), then dried in vacuo at room temperature to give Dibenziodolium, 3,7-dinitro-, hydrogensulfate (10.17 g, 74%).

Dibenziodolium, 3,7-dinitro-, Chloride

To a hot (95-100° C.) suspension of Dibenziodolium, 3,7-dinitro-, hydrogensulfate (10.1 g, 21.7 mmol) in formic acid (88%, 500 mL) was added a solution of potassium chloride (6.59 g, 88.4 mmol) in water (35.0 mL). The reaction mixture immediately became a bright yellow color with precipitation of the chloride salt. The yellow solid was collected by suction filtration, washed with water (1.0 L) and EtOAc (200 mL), then dried in vacuo at 40-50° C. to give Dibenziodolium, 3,7-dinitro-, chloride (8.1 g, 92%), as a yellow powder.

Dibenziodolium, 3,7-diamino-, Chloride

To a stirring suspension of Dibenziodolium, 3,7-dinitro-, chloride (6.00 g, 14.8 mmol) in conc. HCl (60 mL) at room temperature was added tin (II) chloride dihydrate (36.0 g, 159 mmol). The reaction mixture was heated at 80° C. for 10 hours, then allowed to cool to room temperature overnight. The reaction mixture was suction filtered and the brown solid was washed with water (5×50 mL). The solid was dissolved in boiling water (600 mL) and filtered to remove insoluble material. The filtrate was warmed to give a solution and adjusted to pH 8.5 with dilute NH4OH. The resulting suspension was cooled to 5° C. for 3 hours and then suction filtered. The yellow solid was washed with water (5×50 mL) and EtOAc (3×50 mL), then dried in vacuo at 40-50° C. to give Dibenziodolium, 3,7-diamino-, chloride (3.5 g, 68%).

Dibenziodolium, 3,7-diamino-, Methanesulfonate

To a stirring suspension of Dibenziodolium, 3,7-diamino-, chloride (344 mg, 1.00 mmol) in MeOH (240 mL) at room temperature was added silver methanesulfonate (203 mg, 1.00 mmol). The reaction mixture was stirred at room temperature for 7 hours, then filtered by gravity through two fluted papers. The filtrate was concentrated to dryness. The residue was dissolved in a mixture of MeOH (50 mL) and CH2Cl2 (25 mL), then diluted with hexanes (50 mL). The suspension of yellow solid was stored at 5° C. for 3 days, then suction filtered. The solid was washed with hexanes (2×20 mL), and dried in vacuo to give Dibenziodolium, 3,7-diamino-, methanesulfonate (312 mg, 77%); m.p. 225-229° C. (dec)(uncorrected).

Nuclear Magnetic Resonance Spectroscopy:
$^1$H NMR (600 MHz, DMSO-d6): δ 7.71-7.69 (d, 2H); 7.22-7.21 (d, 2H); 6.87-6.85 (dd, 2H); 5.84 (s, 4H); 2.32 (s, 3H).

Mass Spectroscopy:
Method of Ionization: Electrospray (+ve) Calc'd for (C12H10IN2)+=309 Found: m/z (relative intensity) 309 (100%).

Compound 19 Dibenziodolium, 3,7-bis(dimethylamino)-, Iodide and Compound 20

Dibenziodolium, 3,7-bis(dimethyl-amino)-, Methanesulfonate

Dibenziodolium, 3,7-bis(dimethylamino)-, Iodide Dihydroiodide

A solution of iodine (1.05 g, 4.14 mmol) and potassium iodate (2.73 g, 12.76 mmol) in concentrated sulfuric acid (38 mL) was stirred at room temperature for 4.5 hours to give a yellow suspension of iodyl sulfate. The mixture was cooled to −6° C. and a solution of N,N,N',N'-tetramethylbenzidine (5.00 g, 20.8 mmol) in concentrated sulfuric acid (11 mL) was added dropwise keeping the temperature less than or equal to −5° C. The reaction mixture was stirred at −5° C. for 2.0 hours, then poured onto ice (200 g). The solution was treated with sat. aq. NaHSO3 until a negative starch-I2 test was observed. A solution of KI (23.2 g, 140 mmol) in H2O (55 mL) was added and the mixture was allowed to stand at 5° C. for 20 hours. The solid was collected by suction filtration and washed with water (3×50 mL). The solid was triturated in acetone (100 mL), suction filtered, and washed with additional acetone (3×25 mL), then dried in vacuo at 40-50° C. to give Dibenziodolium, 3,7-bis(dimethylamino)-, iodide dihydroiodide (1.8 g, 12%).

Compound 19 Dibenziodolium, 3,7-bis(dimethylamino)-, Iodide

A mixture of Dibenziodolium, 3,7-bis(dimethylamino)-, iodide dihydroiodide (1.8 g, 2.4 mmol) in chloroform (10 mL) and 5% aq. NaOH (20 mL) was stirred at room temperature for 10 hours. The reaction mixture was suction filtered and the solid was washed with water (3×25 mL), EtOH (3×25 mL), and Et2O (4×25 mL). The solid was triturated in a mixture of boiling CHCl3/MeOH (15 mL/6 mL), then suction filtered the hot suspension. The tan solid was dried in vacuo to give Dibenziodolium, 3,7-bis(dimethylamino)-, Iodide (1.1 g, 93%).

Compound 20 Dibenziodolium, 3,7-bis(dimethylamino)-, Methanesulfonate

To a stirring suspension of Dibenziodolium, 3,7-bis(dimethylamino)-, Iodide (451 mg, 0.916 mmol) in methanol (316 mL) was added silver methanesulfonate (186 mg, 0.916 mmol). The reaction mixture was stirred vigorously at room temperature for 20 hours. The reaction mixture was suction filtered, and the filtrate was concentrated to dryness. The residue was suspended in a mixture of CH2Cl2/Et2O (10 mL/150 mL) and then suction filtered. The solid was washed with Et2O (3×25 mL) and dried in vacuo to give Dibenziodolium, 3,7-bis(dimethylamino)-, methanesulfonate (374 mg, 89%); m.p. 232-235° C. (dec)(uncorrected).

Nuclear Magnetic Resonance Spectroscopy:
1H NMR (500 MHz, DMSO-d6): δ 7.93-7.91 (d, 2H); 7.40-7.39 (d, 2H); 7.08-7.06 (dd, 2H); 3.00 (s, 12H); 2.33 (s, 3H).

Mass Spectroscopy:
Method of Ionization: Electrospray (+ve)
Calc'd for (C16H18IN2)+=365 Found: m/z (relative intensity) 365 (100%).

Compound 21 Dibenz[b,d]iodolium, 3-(methoxycarbonyl)-, Salt with 4-methyl-benzenesulfonic Acid (1:1)

Methyl 4-(2-iodophenyl)benzoate

A solution of methyl 4-(2-aminophenyl)benzoate (450 mg, 1.71 mmol) in water (65 mL) and concentrated hydrochloric acid (6.5 mL) chilled to 0-2° C. then an ice-cold solution of sodium nitrite (127 mg, 1.85 mmol) in water (1 mL) was slowly added dropwise while the mixture was slowly stirred. After 15 minutes, a solution of potassium iodide (267 mg, 1.61 mmol) in water (1 mL) was added at 0-5° C. to the light yellow solution with vigorous stirring. The cooling bath was removed and the reaction mixture was allowed to stand at room Temperature for 1 hour. Added a solution of sat. aq. NaHSO3 until a negative Starch-KI paper test was obtained, then added EtOAc (150 mL) and stirred vigorously for 0.5 hour. The mixture was extracted with EtOAc (3×100 mL) and the combined organic layer was washed with water (3×200 mL) and brine (100 mL). The organic layer was dried (Na2SO4), filtered and concentrated to dryness to give crude Methyl 4-(2-iodophenyl)benzoate (444 mg, 69%). An additional reaction was performed to give a total of 1.6 g of crude Methyl 4-(2-iodophenyl)benzoate. The crude was purified by column chromatography on silica gel (60 g, 2.5×25 cm bed volume) eluted with a step gradient from 19:1 to 9:1 hexanes/EtOAc. Fractions containing pure Methyl 4-(2-iodophenyl)benzoate were combined and concentrated to give 2 (707 mg), as an amber oil which solidified on standing at −20° C.

Dibenz[b,d]iodolium, 3-(methoxycarbonyl)-, Salt with 4-methylbenzenesulfonic Acid (1:1)

To a stirring solution of methyl 4-(2-iodophenyl)benzoate (511 mg, 1.36 mmol) in acetonitrile (5.5 mL) was added [hydroxy(tosyloxy)iodo]-benzene (557 mg, 1.36 mmol). The suspension was stirred at room temperature for 7 days. The reaction mixture (white suspension) was suction filtered and the solid was washed with acetonitrile (20 mL). The solid was dried in vacuo at room temperature to give Dibenz[b,d]iodolium, 3-(methoxycarbonyl)-, salt with 4-methylbenzenesulfonic acid (1:1) (272 mg, 37%); m.p.>250° C.

Nuclear Magnetic Resonance Spectroscopy:
$^1$H NMR (500 MHz, DMSO-d6): δ 8.84 (d, 1H); 8.64-8.62 (d, 1H); 8.61-8.59 (dd, 1H); 8.37-8.35 (dd, 1H); 8.30-8.28 (d, 1H); 7.94-7.90 (m, 1H); 7.82-7.78 (m, 1H); 7.50-7.49 (d, 2H); 7.13-7.11 (d, 2H); 3.96 (s, 3H); 2.30 (s, 3H).

Mass Spectroscopy:
Method of Ionization: Electrospray (positive ion) Calc'd for (C14H10IO2)+=337 Found: m/z (relative intensity) 337.1 [100%, (M+H+)].

Compound 22 Dibenziodolium,
3,7-bis[(di-methylamino)methyl]-, iodide
Hydroiodide 4,4'-Bis(dimethylaminomethyl)biphenyl To a solution 4,4'-bis(bromomethyl)biphenyl (3.0 g, 8.8 mmol) in THF (60 mL) at 0-7° C. was bubbled in dimethylamine gas for 10 minutes. The reaction mixture was stirred at room temperature for 3 days. The reaction mixture was diluted with EtOAc (150 mL) and washed with sat. aq. NaHCO$_3$ (100 mL). The aqueous layer was backextracted with EtOAc (2×30 mL) and the combined organic layer was washed with water (50 mL) and brine (50 mL). The organic layer was dried (MgSO4), filtered, and concentrated to give 4,4'-Bis(dimethylaminomethyl)biphenyl (2.35 g, 99%).

Dibenziodolium, 3,7-bis[(dimethylamino)-methyl]-,
iodide Hydroiodide

A solution of iodine (154 mg, 0.594 mmol) and potassium iodate (400 mg, 1.87 mmol) in concentrated sulfuric acid (6.5 mL) was stirred at room temperature for 6 hours to give a yellow suspension of iodyl sulfate. The mixture was cooled to 0° C. and a solution of 4,4'-Bis(dimethylaminomethyl)biphenyl (816 mg, 3.04 mmol) in concentrated sulfuric acid (2 mL) was added dropwise at 0° C. The reaction mixture was stirred at −5 to −10° C. for 2.0 hours. The mixture was poured onto ice (50 g) and sat. aq. NaHSO3 was added dropwise until starch-I2 paper showed a negative test (quench of excess iodyl sulfate). A solution of potassium iodide (5 g) in water (10 mL) was added and a precipitate formed immediately. The suspension was stored at 5° C. for 18 hours, then suction filtered. The solid was washed with water (3×10 mL), and acetone (2×5 mL), then dried in vacuo at 35° C. to give Dibenziodolium, 3,7-bis[(dimethylamino)-methyl]-, iodide hydroiodide (690 mg, 29%); m.p. 192-195° C. (dec, uncorrected).
Nuclear Magnetic Resonance Spectroscopy:
$^1$H NMR (500 MHz, DMSO-d6): δ 10.20-9.50 (bm, ~1.4H); 8.59 (s, 2H); 8.58-8.56 (d, 2H); 7.98-7.96 (d, 2H); 4.38 (s, 4H); 2.74 (s, 12H).
Mass Spectroscopy:
Method of Ionization: Electrospray (+ve) Calc'd for (C18H22IN2)+=393.1 Found: m/z (relative intensity) 393.1 (C$_{18}$H22IN2)+(100%).

Compound 23 Dibenziodolium, 3,7-bis[[[(di-methylamino)methyl]carbonyl]-amino]-, Chloride (~94:6 bisamide:monoamide)

Dibenziodolium, 3,7-dinitro-, Hydrogensulfate

A solution of iodine (1.66 g, 6.54 mmol) and potassium iodate (4.31 g, 20.1 mmol) in concentrated sulfuric acid (17.0 mL) was stirred at room temperature for 6 hours to give a yellow suspension of iodyl sulfate. The mixture was cooled to 5° C. and 4,4'-dinitrobiphenyl (8.00 g, 32.8 mmol) was added. The reaction mixture was warmed to room temperature and then stirred at room temperature for 20 hours. The thick, yellow suspension was poured onto a mix of ice (100 g) and water (100 mL) to give a purple-colored suspension. The suspension was suction filtered and the solid was washed with water (1.0 L). The solid was triturated EtOAc (200 mL) and suction filtered. The solid was washed with EtOAc (3×50 mL), then dried in vacuo at room temperature to give Dibenziodolium, 3,7-dinitro-, hydrogensulfate (13.3 g, 87%), as a light yellow solid.

Dibenziodolium, 3,7-dinitro-, Chloride

To a hot (95-96° C.) solution of Dibenziodolium, 3,7-dinitro-, hydrogensulfate (13.3 g, 28.5 mmol) in formic acid (88%, 500 mL) was added a solution of potassium chloride (8.90 g, 119 mmol) in water (45.0 mL). The reaction mixture immediately became a bright yellow color with precipitation of the chloride salt. The yellow solid was collected by suction filtration, washed with water (4×50 mL) and EtOAc (3×50 mL), then dried in vacuo at room temperature to give Dibenziodolium, 3,7-dinitro-, chloride (9.6 g, 83%), as a light yellow powder.

Dibenziodolium, 3,7-diamino-, Chloride

To a stirring suspension of Dibenziodolium, 3,7-dinitro-, chloride (6.00 g, 14.8 mmol) in conc. HCl (60 mL) at room temperature was added tin (II) chloride dihydrate (36.0 g, 159 mmol). The reaction mixture was heated at 80° C. for 10 hours (Note 1), then allowed to cool to room temperature overnight. The reaction mixture was suction filtered and the solid was washed with water (6×50 mL). The solid was dissolved in boiling water (600 mL) and filtered to remove insoluble material. The filtrate (pH=2) was cooled to room temperature and adjusted to pH 8.5 with dilute NH4OH. The resulting suspension was suction filtered. The yellow solid was washed with water (5×50 mL) and EtOAc (3×50 mL), then dried in vacuo at 40-50° C. to give Dibenziodolium, 3,7-diamino-, chloride (3.1 g, 61%).

Dibenziodolium, 3,7-diamino-, Methanesulfonate

To a stirring suspension of Dibenziodolium, 3,7-diamino-, chloride (688 mg, 2.00 mmol) in MeOH (480 mL) at room temperature was added silver methanesulfonate (406 mg, 2.00 mmol). The reaction mixture was stirred at room temperature for 20 hours, then filtered by gravity through two fluted papers. The filtrate was concentrated to dryness. The residue was dissolved in a mixture of MeOH (25 mL) and CH2Cl2 (15 mL), then diluted with hexanes (50 mL). The suspension of yellow solid was stored at 5° C. for 1 hour, then suction filtered. The solid was washed with hexanes (2×20 mL), and dried in vacuo at room temperature to give Dibenziodolium, 3,7-diamino-, methanesulfonate (696 mg, 86%).

Dibenziodolium, 3,7-bis[[[(dimethylamino)-methyl]
carbonyl]amino]-, Chloride

To a stirring solution of Dibenziodolium, 3,7-diamino-, methanesulfonate (450 mg, 1.11 mmol) in N,N-dimethylformamide (7 mL) at room temperature was added dimethylaminoacetyl chloride hydrochloride (414 mg, 2.23 mmol) and triethylamine (350 μL, 2.51 mmol). After 1.5 hours at room temperature, the TLC (3:1 CH3CN:0.2 M NH4Cl(aq), silica gel) showed the reaction to be ~50% completed. Additional dimethylaminoacetyl chloride hydrochloride (414 mg, 2.23 mmol), triethylamine (350 μL, 2.51 mmol), and N,N-dimethylformamide (1 mL) were added and stirring was continued for 2 hours at room temperature, when the TLC showed that dimethylaminoacetyl chloride hydrochloride was consumed. Water (100 mL) was added to the reaction mixture to give a clear, yellow solution (pH=3). Added 1.0 N HCl until the pH of the mixture was pH=2, then washed the aqueous layer with CH2Cl2 (4×100 mL). The aqueous layer (pH=2) was adjusted to pH=9 with dilute NH4OH (5 mL conc. NH4OH+100 mL deionized water). The resulting suspension was stored at 5° C. for 1 hour, and then suction filtered. The solid was washed with water (25 mL) and EtOAc (2×25 mL). The solid was triturated in acetone (8 mL) at room temperature for 4 hours then suction filtered. The yellow powder was washed with hexanes (10 mL) and dried in vacuo at room temperature. The solid was triturated in MeOH (15 mL) at room temperature for 1 hour. The suspension was suction filtered and the solid was washed with Et2O (3×5 mL). The solid was dried in vacuo at room temperature to give dibenziodolium, 3,7-bis[[[(dimethylamino)-methyl]carbonyl]amino]-, chloride (195 mg, 34%); m.p. 203-206° C. (dec)(uncorrected).
Nuclear Magnetic Resonance Spectroscopy:
$^1$H NMR (500 MHz, DMSO-d6): δ 10.21 (s, 2H); 8.81-8.80 (d, 2H); 8.20-8.19 (d, 2H); 7.98-7.96 (dd, 2H); 3.14 (s, 4H); 2.30 (s, 12H).
Mass Spectroscopy:
Method of Ionization: Electrospray (+ve) Calc'd for (C20H24IN4O2)+=479.1 Found: m/z (relative intensity) 479.1 (55%); 240.1 [(M++H)2+/2](100%); 394.1 (monoamide=($C_{16}$H17IN3O)+(20%); 197.5 (monoamide=[(M++H)2+/2](15%).

Compound 24 Dibenziodolium,
3,7-bis[(di-methylamino)methyl]-, Iodide 4,4'-Bis(dimethylaminomethyl)biphenyl and Dibenziodolium, 3,7-bis[(dimethylamino)-methyl]-, iodide hydroiodide were prepared as for Compound 22 above.

Dibenziodolium, 3,7-bis[[(dimethylamino)-methyl]-, Iodide

To a stirring solution of Dibenziodolium, 3,7-bis[(dimethylamino)-methyl]-, iodide hydroiodide (1.00 g, 1.29 mmol) in CHCl3 (6.5 mL) was added 5% NaOH (aq.)(12.5 mL) and the reaction mixture was stirred at ambient temperature for 20 hours. The reaction mixture was suction filtered and the solid was washed with water (15 mL) and Et2O (100 mL), then dried in vacuo at room temperature to give Dibenziodolium, 3,7-bis[(dimethylamino)-methyl]-, iodide (292 mg, 44%); m.p. 166-169° C. (dec)(uncorrected).
Nuclear Magnetic Resonance Spectroscopy:
$^1$H NMR (500 MHz, DMSO-d6): δ 8.36-8.34 (d, 2H); 8.33 (s, 2H); 7.73-7.71 (d, 2H); 3.55 (s, 4H); 2.21 (s, 12H).
Mass Spectroscopy:
Method of Ionization: Electrospray (+ve) Calc'd for (C18H22IN2)+=393.1 Found: m/z (relative intensity) 393.0 ($C_{18}$H22IN2)+(100%).

Compound 31 Iodonium, 3-nitrophenyl-2-thienyl-,
Salt with 4-methylbenzenesulfonic Acid (1:1)

1-Iodo-3-nitrobenzene Diacetate

To a stirring solution of 1-iodo-3-nitrobenzene (4.98 g, 20.0 mmol) in glacial acetic acid (200 mL) at 35-37° C. under argon was slowly added sodium perborate tetrahydrate (31.8 g, 207 mmol), portionwise over 25 minutes. When the addition was completed, the reaction mixture was heated at 40° C. for 20 hours. After cooling to room temperature, the reaction mixture was concentrated to dryness. The residue was partitioned between water (250 mL) and dichloromethane (250 mL). the aqueous layer was extracted with dichloromethane (3×150 mL), and the combined organic layer was washed with water (200 mL), dried (Na2SO4), and concentrated to dryness. The residue was dissolved in a minimum volume of dichloromethane and then added dropwise to stirring hexanes (250 mL). The resulting precipitate was collected by suction filtration, washed with hexanes (50 mL), and dried in vacuo to give 1-Iodo-3-nitrobenzene diacetate (4.77 g, 65%).

1-[Hydroxy(tosyloxy)iodo]-3-nitrobenzene

To a stirring solution of 1-Iodo-3-nitrobenzene diacetate (1.836 g, 5.00 mmol) in acetonitrile (20.0 mL) was added a solution of ptoluenesulfonic acid monohydrate (1.903 g, 10.0 mmol) in acetonitrile (20.0 mL). The resulting white slurry was stirred at room temperature for 20 minutes, then suction filtered. The solid was washed with CH3CN (30 mL) and Et2O (30 mL), then dried in vacuo to give 1-[Hydroxy(tosyloxy)iodo]-3-nitrobenzene (2.05 g, 95%).

Iodonium, 3-nitrophenyl-2-thienyl-, Salt with
4-methylbenzenesulfonic Acid (1:1)

To a solution of 1-[Hydroxy(tosyloxy)iodo]-3-nitrobenzene (600 mg, 1.37 mmol) in glacial acetic acid (5.5 mL) at room temperature was added dropwise thiophene (115.5 mg, 1.37 mmol). After stirring at room temperature for 20 minutes, the reaction mixture was added dropwise to stirring Et2O (200 mL). After stirring at room temperature for 15 minutes, the precipitate was collected by suction filtration, washed with Et2O (30 mL), and dried in vacuo at room temperature to give Iodonium, 3-nitrophenyl-2-thienyl-, salt with 4-methylbenzenesulfonic acid (1:1) (489 mg, 71%); m.p. 136-138° C. (uncorrected).
Nuclear Magnetic Resonance Spectroscopy:
$^1$H NMR (500 MHz, DMSO-d6): δ 9.16 (s, 1H); 8.64-8.63 (d, 1H); 8.45-8.43 (m, 1H); 8.15-8.14 (d, 1H); 8.00-7.99 (d, 1H); 7.83-7.79 (t, 1H); 7.47-7.46 (d, 2H); 7.22-7.20 (t, 1H); 7.11-7.09 (d, 2H); 2.28 (s, 3H).
Mass Spectroscopy:
Method of Ionization: Electrospray (+ve) Calc'd for (C10H7INO2S)+=332 Found: m/z (relative intensity) 332 (100%).

Compound 33 Iodonium, phenyl(5-iodo-4-phenyl-2-thienyl)-, Salt with 4-methylbenzenesulfonic Acid (1:1)

2-Iodo-3-phenylthiophene

To a stirring solution of 3-phenylthiophene (1.35 g, 8.43 mmol) in chloroform (22 mL) and glacial acetic acid (22 mL) at room temperature was added N-iodosuccinimide (2.00 g, 8.45 mmol). The reaction mixture was stirred at room temperature for 2 hours. The mixture was diluted with water (44 mL) and the organic layer was separated and washed with water (100 mL), 2% aq. KOH (100 mL) and water (100 mL). The organic layer was dried over MgSO4, filtered and concentrated to dryness to give crude 2 (2.4 g, 100%) as a yellow oil. The crude material was purified on a column of silica gel (150 g, 4.5×25 cm) eluted with hexanes to give pure product (1.37 g, 57%).

Iodonium, phenyl(5-iodo-4-phenyl-2-thienyl)-, Salt with 4-methylbenzenesulfonic Acid (1:1)

To a stirring solution of 2-iodo-3-phenylthiophene (604 mg, 2.11 mmol) in glacial acetic acid (8.4 mL) at room temperature was added [hydroxy(tosyloxy)iodo]benzene (863 mg, 2.11 mmol, 96%). The reaction mixture was stirred at room temperature for 30 minutes to give a yellow solution. The reaction mixture was added slowly dropwise to stirring Et2O (175 mL) at room temperature to give a white precipitated solid. The suspension was stirred at room temperature for 30 minutes and then the solid was collected by suction filtration. The white solid was washed with Et2O (80 mL) and dried in vacuo at 35° C. to give Iodonium, phenyl(5-iodo-4-phenyl-2-thienyl)-, salt with 4-methylbenzenesulfonic acid (1:1) (1.15 g, 83%); m.p. 169-171° C. (dec)(uncorrected).

Nuclear Magnetic Resonance Spectroscopy:
1H NMR (500 MHz, DMSO-d6): δ 8.32-8.30 (d, 2H); 8.00 (s, 1H); 7.71-7.68 (t, 1H); 7.58-7.55 (t, 2H); 7.51-7.42 (m, 7H); 7.11-7.09 (d, 2H); 2.28 (s, 3H).

Mass Spectroscopy:
Method of Ionization: Electrospray (positive ion) Calc'd for (C16H11I2S)+=488.9 Found: m/z (relative intensity) 488.9 (100%).

Compound 38 10H-Dibenz[b,e]iodinium, 3,7-bis(dimethylamino)-, Methanesulfonate

10H-Dibenz[b,e]iodinium, 3,7-bis(dimethylamino)-, Iodide, Dihydroiodide

A solution of iodine (770 mg, 2.97 mmol) and potassium iodate (2.00 g, 9.34 mmol) in concentrated sulfuric acid (28.0 mL) was stirred at room temperature for 5 hours to give a yellow suspension of iodyl sulfate. The mixture was cooled to −10 to −15° C. and a solution of 4,4'-methylenebis(N,N-dimethylaniline) (3.866 g, 15.2 mmol) in conc. sulfuric acid (7.6 mL) was added, keeping the temperature below −5° C. The reaction mixture was stirred at −5° C. for 1.5 hours, then poured onto crushed ice (250 g) and sat. aq. NaHSO3 was added until a negative starch-I2 test was obtained. A solution of potassium iodide (17.0 g, 102 mmol) in water (40.0 mL) was added and the resulting suspension was allowed to stand at 5° C. for two days. The suspension was suction filtered and the solid was washed with water (4×50 mL) and acetone (4×50 mL). The solid was triturated with acetone (15 mL) and suction filtered. The solid was washed with acetone (2×15 mL) and dried in vacuo at room temperature to give 10H-dibenz[b,e]iodinium, 3,7-bis(dimethylamino)-, iodide, dihydroiodide (4.9 g, 42%).

10H-Dibenz[b,e]iodinium, 3,7-bis(dimethylamino)-, Iodide

To a suspension of 10H-dibenz[b,e]iodinium, 3,7-bis(dimethylamino)-, iodide, dihydroiodide (2.4 g, 3.15 mmol) in chloroform (12 mL) was added a solution of sodium hydroxide in water (5%, 22 mL). The reaction mixture was stirred vigorously at room temperature for 10 hours. The solid was collected by suction filtration, washed with EtOH (3×10 mL), water (3×10 mL) and EtOH (25 mL), then dried in vacuo at 50° C. to give 10H-dibenz[b,e]iodinium, 3,7-bis(dimethylamino)-, iodide (1.5 g, 94%); m.p. 210-212° C. (dec)(uncorrected)(lit. m.p. 195.5° C.).

10H-Dibenz[b,e]iodinium, 3,7-bis(dimethylamino)-, Methanesulfonate

To a stirring suspension of 10H-dibenz[b,e]iodinium, 3,7-bis(dimethylamino)-, iodide (506 mg, 1.00 mmol) in methanol (350 mL) was added silver methanesulfonate (203 mg, 1.00 mmol). The reaction mixture was stirred vigorously at room temperature for 5 hours. The reaction mixture was suction filtered, and the filtrate was concentrated to dryness. The residue was coevaporated with Et2O (2×5 mL) and the solid was dried in vacuo to give 10H-Dibenz[b,e]iodinium, 3,7-bis(dimethylamino)-, methanesulfonate (420 mg, 89%); m.p. 192-194° C. (dec)(uncorrected).

Nuclear Magnetic Resonance Spectroscopy:
1H NMR (500 MHz, DMSO-d6): δ 7.50-7.49 (d, 2H); 7.38-7.37 (d, 2H); 6.89-6.87 (dd, 2H); 3.97 (s, 2H); 2.91 (s, 12H), 2.31 (s, 3H).

Mass Spectroscopy:
Method of Ionization: Electrospray (+ve) Calc'd for (C17H20IN2)+=379 Found: m/z (relative intensity) 379.2 (100%).

Compound 41 [1,4]Iodoxino[2,3-f:6,5-f]diquinolin-14-ium, Iodide and Compound 42

[1,4]Iodoxino[2,3f::6,5-f']-diquinolin-14-ium, Methane-Sulfonate

6,6'-Oxydiquinoline

To a stirring suspension of 4,4'-oxydianiline (14.0 g, 69.9 mmol), glycerol (45.0 mL, 617 mmol), and nitrobenzene (8.4 mL) at room temperature under argon, was added concentrated sulfuric acid (28.0 mL). The mixture exothermed to ~80° C., and then was carefully heated to 135° C. The mixture began to vigorously reflux and the temperature rose to 150° C. The heating source was removed and the temperature was allowed to cool back to 135° C. Heating at reflux (135° C.) was continued for 3 hours. After cooling to room temperature, water (150 mL) was added and the mixture was cooled to 5-10° C. The pH of the mixture was adjusted to pH 10 with 20% aq. NaOH. The thick, dark brown gum that formed was washed with water (4×150 mL), and then extracted by trituration with warm (50° C.) EtOAc (4×250 mL). The combined organic layer (dark yellow solution) was washed with water (200 mL), dried (Na2SO4), filtered, and concentrated to dryness. The residue was dissolved in 1.0 N HCl (aq)(50.0 mL). The solution was treated with activated carbon (0.5 g), heated to ~60° C., and the warm suspension was suction filtered through a pad of GFA paper (Whatman). The filtrate was adjusted to pH 9-10 (dilute NH4OH) to precipitate a brown gum. The water was decanted off, and the gum was dissolved in Et2O (800 mL), dried (Na2SO4), filtered, and concentrated in vacuo to give a dark red oil (6 g). The oil was dissolved in EtOAc (25 mL) and purified on a column of silica gel (300 g, 5×38 cm) eluted with EtOAc (2 L) and EtOAc/MeOH (19:1) to give pure 6,6'-Oxydiquinoline (4.4 g, 23%), as a red solid.

[1,4]Iodoxino[2,3-f:6,5-f']diquinolin-14-ium, Iodide, Dihydroiodide

A solution of iodine (193 mg, 0.76 mmol) and potassium iodate (510 mg, 2.38 mmol) in concentrated sulfuric acid (7.0 mL) was stirred at room temperature for 5 hours to give a yellow suspension of iodyl sulfate. The mixture was cooled to −10 to −15° C. and a solution of 6,6'-Oxydiquinoline (1.06 g, 3.89 mmol) in conc. sulfuric acid (2.0 mL) was added, keeping the temperature below −5° C. The reaction mixture was stirred at −5° C. for 1.5 hours, then poured onto crushed ice (250 g) and sat. aq. NaHSO3 was added until a negative starch-I2 test was obtained. A solution of potassium iodide (4.25 g, 25.6 mmol) in water (10.0 mL) was added and the resulting suspension was allowed to stand at 5° C. for two days. The suspension was suction filtered and the solid was washed with water (350 mL) and acetone (4×25 mL). The solid was triturated with acetone (150 mL) and suction filtered. The solid was washed with acetone (2×15 mL) and dried in vacuo at room temperature to give [1,4]Iodoxino[2,3-f:6,5-f]diquinolin-14-ium, iodide, dihydroiodide (1.4 g, 46%).

[1,4]Iodoxino[2,3-f:6,5-f']diquinolin-14-ium, Iodide

To a suspension of [1,4]Iodoxino[2,3-f:6,5-f']diquinolin-14-ium, iodide, dihydroiodide (1.325 g, 1.69 mmol) in chloroform (8 mL) was added a solution of sodium hydroxide in water (5%, 16 mL). The reaction mixture was stirred vigorously at room temperature for 10 hours. The solid was collected by suction filtration, washed with EtOH (4×25 mL), water (4×25 mL) and EtOH (3×15 mL), then dried in vacuo at 40° C. to give compound 41[1,4]Iodoxino[2,3-f:6,5-f']diquinolin-14-ium, iodide, (677 mg, 76%); m.p. 178-181° C. (dec)(uncorrected)(lit. m.p. 221-222° C.).

[1,4]Iodoxino[2,3-f:6,5-f']diquinolin-14-ium, methanesulfonate

A suspension of [1,4]Iodoxino[2,3-f:6,5-f']diquinolin-14-ium, iodide (0.4125 g, 0.787 mmol) and silver methanesulfonate (0.1597 g, 0.787 mmol) in methanol (230 mL) was stirred vigorously at room temperature for 20 hours. The reaction mixture was filtered and the residue of silver iodide was washed with methanol (3×15 mL). The combined filtrate and washings was concentrated to dryness. The residual solid was triturated with Et2O/MeOH (4:1, 15 mL) for 45 minutes, then suction filtered. The yellow solid was washed with Et2O (3×10 mL) and dried in vacuo to give crude product (345 mg). The crude material was dissolved in CHCl3/MeOH (10 mL/1 mL), spin-evaporated to ~1-2 mL (thick oil), and then diluted with Et2O (50 mL). The precipitated solid was collected by suction filtration, washed with Et2O (15 mL), and dried in vacuo to give [1,4]Iodoxino[2,3-f:6,5-f']diquinolin-14-ium, methanesulfonate (310 mg, 80%); m.p. 219-221° C. (dec)(uncorrected).
Nuclear Magnetic Resonance Spectroscopy:
1H NMR (500 MHz, DMSO-d6): δ 9.05-9.03 (dd, 2H); 8.53-8.51 (d, 2H); 8.40-8.38 (d, 2H); 8.28-8.26 (d, 2H); 7.86-7.83 (dd, 2H); 2.30 (s, 3H).
Mass Spectroscopy:
Method of Ionization: Electrospray (+ve) Calc'd for (C18H10IN2O)+=397 Found: m/z (relative intensity) 397.0 (100%).

Compound 43 Iodonium, (2-phenylimidazo-[1,2-a]pyridin-3-yl)phenyl-, Salt with 4-methylbenzenesulfonic Acid (1:1)

A mixture of imidazo[1,2-a]pyridine,2-phenyl- (200 mg, 1.03 mmol) and [hydroxy(tosyloxy)iodo]benzene (96%, 422 mg, 1.03 mmol) in acetone (8 mL) was stirred at room temperature under an argon atmosphere for 4 hours. Initially, the reaction mix is a yellow solution but after 30 minutes a white precipitate formed. Additional acetone (3 mL) was added and stirring was continued. After 4 hours the suspension was diluted with Et2O (400 mL) and the solid was collected by suction filtration. The solid was washed with Et2O (100 mL) and dried in vacuo at room temperature to give the product (498 mg, 85%); m.p. 119-122° C.
Nuclear Magnetic Resonance Spectroscopy:
1H NMR (600 MHz, DMSO-d6): δ 9.11-9.10 (d, 1H); 7.91-7.90 (d, 2H); 7.87-7.84 (m, 3H); 7.64-7.57 (m, 5H); 7.46-7.43 (m, 4H); 7.32-7.30 (t, 1H); 7.11-7.09 (d, 2H); 2.28 (s, 3H).
Mass Spectroscopy:
Method of Ionization: Electrospray (positive ion) Calc'd for (C19H14IN2)+=397.0 Found: m/z (relative intensity) 397.3 (100%, M+).

Compound 44 Iodonium, [2-(4-fluorophenyl)-imidazo[1,2-a]pyridin-3-yl]phenyl-, Salt with 4-methylbenzenesulfonic Acid (1:1)

Imidazo[1,2-a]pyridazine, 2-(4-fluorophenyl)-

A mixture of 2-aminopyridine (2.17 g, 23.06 mmol) and 2-bromo-4'-fluoroacetophenone (5.00 g, 23.04 mmol) in EtOH (46 mL) was heated at reflux for 4 hours. The reaction mixture was cooled to 45° C. and potassium carbonate (3.33 g, 24.1 mmol) was added. The reaction mixture was heated at reflux for 4 hours, then cooled to ambient temperature and stirred overnight. The reaction mixture was concentrated to dryness and the residue was partitioned between water (200 mL) and EtOAc (200 mL). The organic layer was separated, washed with water (3×250 mL) and brine (250 mL) and then dried (MgSO4), filtered and concentrated to dryness. The residual solid was dissolved in warm EtOAc (25 mL) then cooled to room temperature and diluted with hexanes (400 mL). The precipitated solid was collected by suction filtration and washed with hexanes (2×15 mL) and a mix of hexanes/EtOAc (20 mL/5 mL). The solid was dried in vacuo at room temperature to give imidazo[1,2-a]pyridazine, 2-(4-fluorophenyl)- (1.37 g, 28%). The combined filtrate and washes were combined and concentrated to dryness. The residue was dissolved in EtOAc (15 mL) and diluted with hexanes (300 mL). The precipitated solid was collected by suction filtration and washed with hexanes (2×15 mL) and dried in vacuo at room temperature to give a second crop of product (650 mg). Total yield was 2.02 g (41%).

Iodonium, [2-(4-fluorophenyl)imidazo[1,2-a]-pyridin-3-yl]phenyl-, Salt with 4-methylbenzenesulfonic Acid (1:1)

A mixture of imidazo[1,2-a]pyridazine, 2-(4-fluorophenyl)- (260 mg, 1.22 mmol) and [hydroxy(tosyloxy)iodo]benzene (96%, 500 mg, 1.22 mmol) in acetone (10 mL) was stirred at room temperature under an argon atmosphere for 4 hours. The thick suspension was diluted with Et2O (265 mL) and the solid was collected by suction filtration. The solid was washed with Et2O (3×50 mL) and dried in vacuo at room temperature to give crude product (625 mg). The crude product was triturated in acetone (15 mL) for 1 hour at room temperature, then collected by suction filtration and washed with acetone (3×10 mL). The solid was dried in vacuo at room temperature for 5 hours to give Iodonium, [2-(4-fluorophenyl)imidazo[1,2-a]-pyridin-3-yl]phenyl-, salt with 4-methylbenzenesulfonic acid (1:1) (553 mg, 79%); m.p. 137-138° C. (dec)(uncorrected).

Nuclear Magnetic Resonance Spectroscopy:

1H NMR (500 MHz, DMSO-d6): δ 9.09-9.08 (d, 1H); 7.97-7.94 (m, 2H); 7.89-7.87 (d, 2H); 7.83-7.82 (d, 1H); 7.63-7.57 (m, 2H); 7.49-7.42 (m, 6H); 7.32-7.29 (m, 1H); 7.10-7.09 (d, 2H); 2.28 (s, 3H).

Mass Spectroscopy:

Method of Ionization: Electrospray (positive ion) Calc'd for (C19H13FIN2)+=415 Found: m/z (relative intensity) 415 (100%, M+).

Compound 45 Iodonium, (2-hydroxy-4,4-di-methyl-6-oxo-1-cyclohexen-1-yl)-2-thienyl-, Salt with 4-methyl-benzenesulfonic Acid (1:1)

2-(Diacetoxyiodo)thiophene and 2-[hydroxy(tosyloxy)iodo]thiophene were prepared according to the procedure for Compound 12 above.

Iodonium, (2-hydroxy-4,4-dimethyl-6-oxo-1-cyclohexen-1-yl)-2-thienyl-, Salt with 4-ethylbenzenesulfonicacid (1:1)

To a stirring suspension of 2-[hydroxy(tosyloxy)iodo]thiophene (298 mg, 0.748 mmol) in CHCl3 (5.5 mL) was added a solution of dimedone (105 mg, 0.749 mmol) in CHCl3 (2.0 mL). The reaction mixture became a yellow solution and was stirred at room temperature for 30 minutes. The golden-yellow solution was added to stirring Et2O (100 mL) to give a precipitate. After 2 hours at −20° C., the suspension was suction filtered and the solid was washed with Et2O (50 mL) and dried in vacuo at room temperature to give Iodonium, (2-hydroxy-4,4-dimethyl-6-oxo-1-cyclohexen-1-yl)-2-thienyl-, salt with 4-ethylbenzenesulfonicacid (1:1) (290 mg, 74%).

Nuclear Magnetic Resonance Spectroscopy:

1H NMR (500 MHz, DMSO-d6): δ 7.79-7.78 (dd, 1H); 7.56-7.55 (dd, 1H); 7.49-7.47 (d, 2H); 7.27-7.26 (d, 2H); 7.12-7.02 (m, 1H); 6.03-5.76 (bm, 1H+H2O); 2.33 (s, 4H); 2.29 (s, 3H); 0.94 (s, 6H).

Mass Spectroscopy:

Method of Ionization: Electrospray (+ve) Calc'd for (C12H14IO2S)+=348.9 Found: m/z (relative intensity) 348.9 (100%).

Compound 46 Iodonium, (2-hydroxy-3-methoxy-carbonyl-4,4-dimethyl-6-oxo-1-carbonyl-4,4-dim-ethyl-6-oxo-1- Salt with 4-methylbenzenesulfonic Acid (1:1)

2-(Diacetoxyiodo)thiophene and 2-[hydroxy(tosyloxy)iodo]thiophene were prepared according to the procedure for Compound 12 above.

Iodonium, (2-hydroxy-3-methoxycarbonyl-4,4-dimethyl-6-oxo-1-cyclohexen-1-yl)-2-thienyl-, Salt with 4-methylbenzenesulfonic Acid (1:1)

To a stirring suspension of 2 (798 mg, 2.00 mmol) in CHCl3 (20.0 mL) was added a solution of methyl 2,2-dimethyl-4,6-dioxocyclohexanecarboxylate (3) (397 mg, 2.00 mmol) in CHCl3 (6.00 mL). The reaction mixture became a yellow solution and was stirred at room temperature for 30 minutes. The golden-yellow solution was added to stirring Et2O (250 mL) to give a precipitate. The suspension was suction filtered and the solid was washed with Et2O (4×25 mL) and dried in vacuo at room temperature to give product (606 mg, 52%); m.p.113-114° C. (uncorrected).

Nuclear Magnetic Resonance Spectroscopy:

1H NMR (500 MHz, DMSO-d6): δ 7.79-7.77 (dd, 1H); 7.51-7.50 (dd, 1H); 7.49-7.47 (d, 2H); 7.12-7.10 (d, 2H); 7.03-7.01 (dd, 1H); 4.69 (bm, 1H); 3.59 (s, 3H); 3.28 (s, 1H); 2.56-2.24 (dd, 2H); 2.29 (s, 3H); 0.97 (s, 3H); 0.96 (s, 3H).

Mass Spectroscopy:

Method of Ionization: Electrospray (+ve) Calc'd for (C14H16IO4S)+=406.98 Found: m/z (relative intensity) 406.9 (100%).

Compound 47 Iodonium, [2-hydroxy-3-(3-methyl-5-isoxazolyl)-4,4-dimethyl-6-oxo-1-cyclohexen-1-yl]-2-thienyl-, Salt with 4-methylbenzenesulfonic Acid (1:1)

2-(Diacetoxyiodo)thiophene and 2-[hydroxy(tosyloxy)iodo]thiophene were prepared according to the procedure for Compound 12 above.

Ethyl 3-methyl-5-isoxazoleacetate

A solution of anhydrous hydrogen chloride in ethyl alcohol was prepared by dissolving acetyl chloride (2.0 mL, 28.1 mmol) in EtOH (40 mL) at room temperature. To the warm solution was added 3 (2.50 g, 17.7 mmol) and the mixture was heated at reflux for 3.5 hours. The reaction mixture was cooled to room temperature and diluted with CH2Cl2 (200 mL). The mixture was washed with sat. aq. NaHCO3 (3×100 mL), dried over Na2SO4, filtered and concentrated to give crude 4 (2.8 g), as a brown liquid. The crude material was purified on a pad of silica gel (100 g on a sintered glass funnel: medium porosity, 350 mL size, 9.5×7.5 cm) eluted with 1:4 EtOAc/hexanes to give pure Ethyl 3-methyl-5-isoxazoleacetate (2.5 g, 83%).

1,3-Cyclohexanedione, 5,5-dimethyl-4-(3-methyl-5-isoxazolyl)-

A solution of sodium ethoxide in ethyl alcohol was prepared by dissolving sodium metal (356 mg, 15.5 mmol) in EtOH (15.0 mL) at room temperature. A solution of Ethyl 3-methyl-5-isoxazoleacetate (2.50 g, 14.8 mmol) in EtOH (5.0 mL) was added and the mixture was stirred at room temperature for 0.5 hour, then mesityl oxide (16.5 mL, 145 mmol) was added dropwise at room temperature. After 1 hour at room temperature, the reaction mixture was heated at reflux for 4 hours. The mixture was cooled to room temperature and concentrated to dryness to give a thick oil. the oil was dissolved in H2O (125 mL) and washed with CHCl3 (2×125 mL). The aqueous layer was acidified to pH 2-3 with 1 N HCl and then extracted with CHCl3 (3×125 mL). The combined organic layer was washed with H2O (100 mL), dried over MgSO4, filtered and concentrated to give a light yellow, oily foam. Triturated with Et2O (150 mL) at room temperature to give a suspension of a white powder. Suction filtered and washed the solid with Et2O (3×25 mL). The white solid was dried in vacuo at room temperature to give 1,3-Cyclohexanedione, 5,5-dimethyl-4-(3-methyl-5-isoxazolyl)- (2.06 g, 63%).

Iodonium, [2-hydroxy-3-(3-methyl-5-isoxazolyl)-4,4-dimethyl-6-oxo-1-cyclohexen-1-yl)-2-thienyl-, Salt with 4-methylbenzenesulfonic Acid (1:1)

To a stirring suspension of 2-[Hydroxy(tosyloxy)iodo]thiophene (773 mg, 1.94 mmol) in CHCl3 (14.0 mL) was added a solution 1,3-Cyclohexanedione, 5,5-dimethyl-4-(3- methyl-5-isoxazolyl)- (143 mg, 1.94 mmol) in CHCl3 (12.0 mL). The reaction mixture was stirred at room temperature for 40 minutes. The reaction mixture was filtered and then was added to stirring Et2O (200 mL) to give a white precipitate. The suspension was suction filtered and the solid was washed with Et2O (4×20 mL) and dried in vacuo at room temperature to give Iodonium, [2-hydroxy-3-(3-methyl-5-isoxazolyl)-4,4-dimethyl-6-oxo-1-cyclohexen-1-yl)-2-thienyl-, salt with 4-methylbenzenesulfonic acid (1:1) (866 mg, 74%); m.p. 118-120° C. (uncorrected).

Nuclear Magnetic Resonance Spectroscopy:

1H NMR (500 MHz, DMSO-d6): δ 7.79-7.78 (dd, 1H); 7.53-7.52 (dd, 1H); 7.49-7.47 (d, 2H); 7.12-7.10 (d, 2H); 7.04-7.02 (dd, 1H); 5.93 (s, 1H); 4.97 (bs, 1H+H2O); 3.74 (s, 1H); 2.46-2.29 (dd, 2H); 2.29 (s, 3H); 2.17 (s, 3H); 0.97 (s, 3H); 0.82 (s, 3H).

Mass Spectroscopy: Method of Ionization: Electrospray (+ve) Calc'd for (C16H17INO3S)+=429.99 Found: m/z (relative intensity) 429.9 (100%).

Compound 48 Iodonium, (2-phenylimidazo-[1,2-a]pyridin-3-yl)thienyl-, Salt with 4-methylbenzenesulfonic Acid (1:1)

2-(Diacetoxyiodo)thiophene and 2-[Hydroxy(tosyloxy) iodo]thiophene were prepared according to the same process as described for Compound 7.

Iodonium, (2-phenylimidazo[1,2-a]pyridin-3-yl)thienyl-, Salt with 4-methylbenzenesulfonic Acid (1:1)

A suspension of 2-[Hydroxy(tosyloxy)iodo]thiophene (715 mg, 1.79 mmol) and imidazo[1,2-a]pyridine,2-phenyl- (348 mg, 1.79 mmol) in acetone (30 mL) was stirred at room temperature for 4 hours. The initial white suspension became a thick, yellow suspension, which after 4 hours had become a much thinner, off-white suspension. The reaction mixture was added to stirring Et2O (800 mL) and the solid was collected by suction filtration. The solid was washed with Et2O (50 mL) and dried in vacuo at room temperature to give crude product (687 mg, 67%). The crude material was triturated in acetone (11 mL) for 15 minutes at room temperature and then the solid was collected by suction filtration. The solid was dried in vacuo at room temperature to give Iodonium, (2-phenylimidazo[1,2-a]pyridin-3-yl)thienyl-, salt with 4-methylbenzenesulfonic acid (1:1) (425 mg, 41%); m.p. 120-121° C. (dec)(uncorrected).

Nuclear Magnetic Resonance Spectroscopy:

1H NMR (500 MHz, DMSO-d6): δ 9.16-9.15 (d, 1H); 7.94-7.92 (d, 2H); 7.86-7.82 (m, 3H); 7.67-7.58 (m, 4H); 7.47-7.45 (d, 2H); 7.36-7.33 (t, 1H); 7.10-7.07 (m, 3H); 2.28 (s, 3H).

Mass Spectroscopy:

Method of Ionization: Electrospray (positive ion) Calc'd for (C17H12IN2S)+=403 Found: m/z (relative intensity) 403.2 (100%).

Example 2

The compounds from Table 1 were subjected to a variety of studies including:

Growth inhibition of HT-29 human colon cancer cells by MTT assay: 48 hr drug exposures over several orders of concentration;

Chemiluminescent measurement of effect of analogs on O2-production by PMA-treated (phorbol myristate acetate, 200 nM) HT-29 human colon cancer cells;

ROS formation also measured using analytical cytometry (inhibition of DCF production from DCFH-DA in HT-29 human colon cancer cells pretreated with agents for 24 hr);

NOX1 and other gene expression by quantitative RT-PCR and Western analysis;

Mitochondrial ROS by analytical cytometry; and

Inhibition of NOX isoform activity in cellular models for NOX1, NOX2, NOX4, NOX5, and Duox2.

Many of the compounds were more growth inhibitory than the parent compounds DPI and DTI; had equivalent or improved ROS inhibition; blocked NOX1 expression; had minimal effect on MT ROS; and clear inhibitory effects in cellular models of NOX activity.

The compounds were analyzed for growth inhibition of HT-29 human colon cancer cells by MTT assay: 48 hr, drug exposures over several orders of concentration. The MTT assay was performed as described in Wu et al J. Immunology 190: 1859-1872, 2013. The results of the assay for several of the compounds are shown in FIGS. 1 (DPI analogs) and 2 (DTI analogs).

Figure 3:
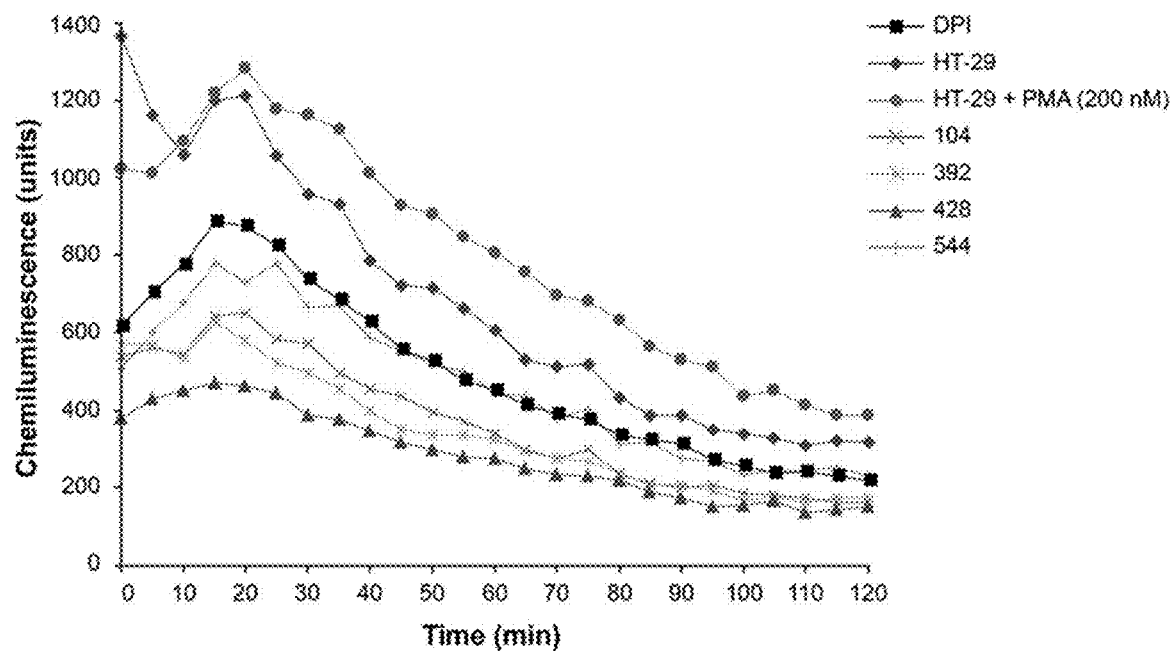
FIG. 3 illustrates the inhibition of superoxide production by the DPI analogs in HT-29 human colon cancer cells (24 hour pretreatment at 250 nM).

FIG. 3 illustrates the inhibition of superoxide production by the DPI analogs in HT-29 human colon cancer cells (24 hour pretreatment at 250 nM).

Figure 4:
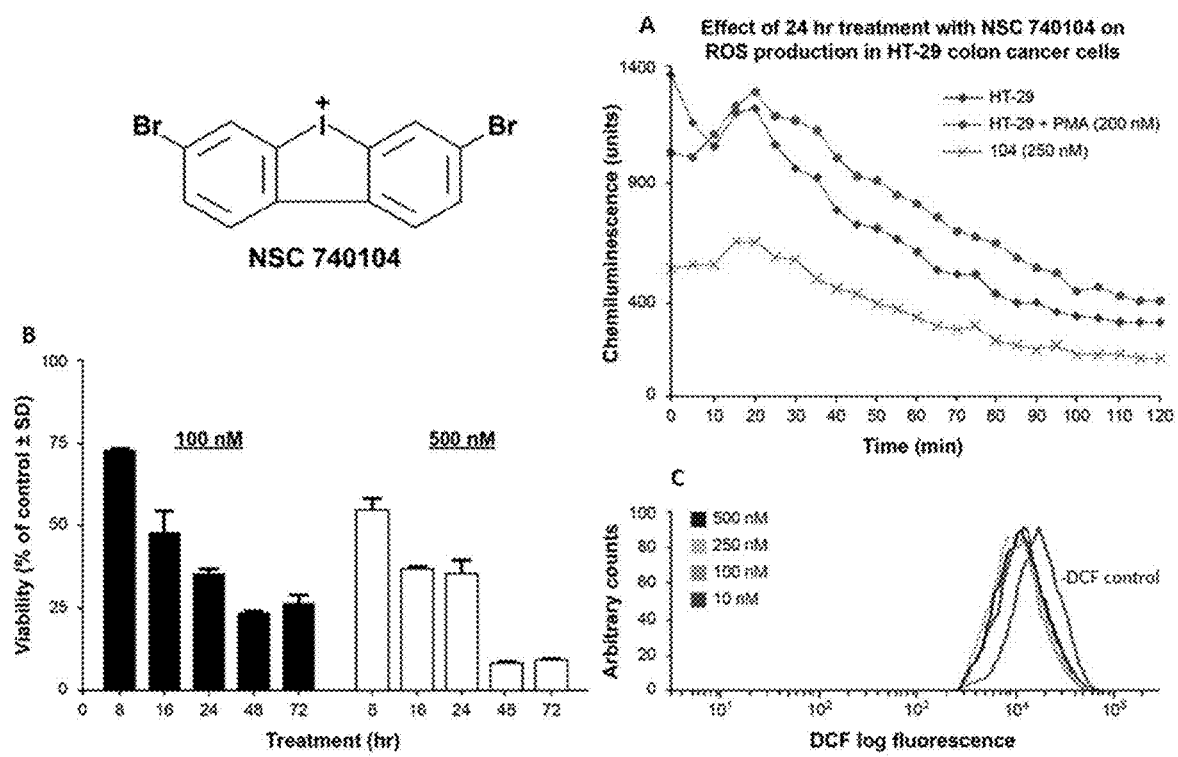
FIGS. 4A, 4B, and 4C illustrate the effect of iodonium analog compound 16 740104 on reactive oxygen production and proliferation in HT-29 human colon cancer cells.

FIGS. 4A, 4B, and 4C illustrate the effect of compound 16 740104 on reactive oxygen production and proliferation in HT-29 human colon cancer cells.

Figure 5:
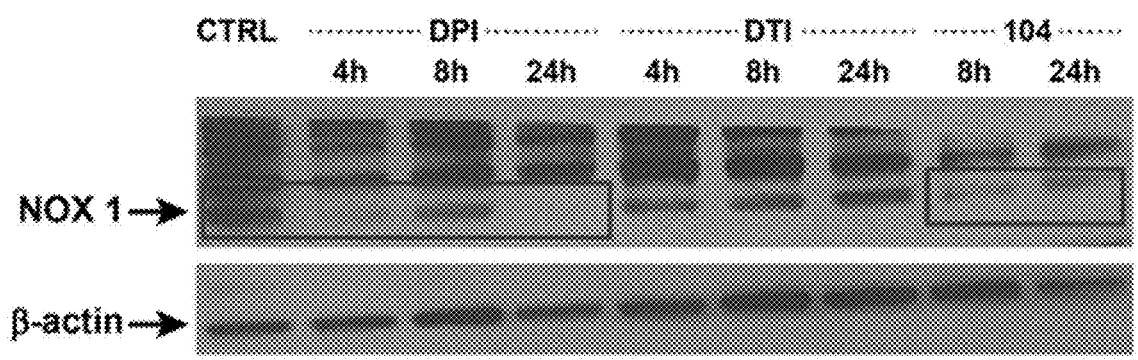
FIG. 5 illustrates the effect of DPI and iodonium analog compound 16 740104 (250 nM) and DTI (10 μM) on NOX1 expression in HT-29 human colon cancer cells.

FIG. 5 illustrates the effect of DPI and compound 16 740104 (250 nM) and DTI (10 μM) on NOX1 expression in HT-29 human colon cancer cells.

Figure 6:
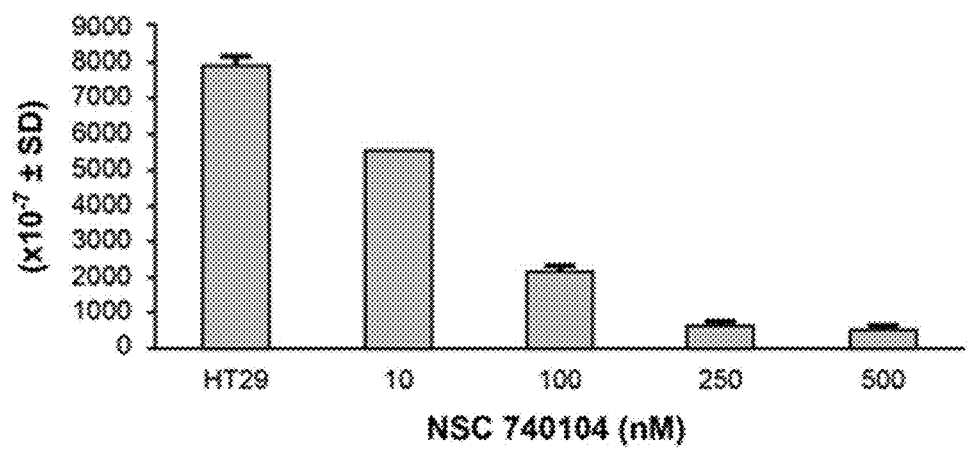
FIG. 6 illustrates NOX1 expression in HT-29 human colon cancer cells, effect of iodonium analog compound 16 740104, concentration (24 hour).

FIG. 6 illustrates NOX1 expression in HT-29 human colon cancer cells, effect of compound 16 740104 Concentration (24 hour).

DPI and five DPI analogs, compounds 16, 14, 24, 21, and 15 (NSCs 740104, 734428, 742837, 751140, 737392), strongly inhibited HT-29 human colon cancer cell growth in a dose dependent manner (IC50's after 48 hr drug exposure of 300, 50, 74, 87, 148, and 202 nM, respectively). Treatment for 24 hr with 10 nM DPI, compounds 16, 14, 21 (740104, 734428, or 751140), or with 100 nM compound 15 (737392) significantly decreased ROS production in HT-29 cells. In addition, 60% or greater inhibition of NOX1 mRNA expression was observed following treatment with 250 nM compound 16 (740104) and compound 14 (734428) for 4 hr; compound 21 (751140) and DPI for 24 hr; and compound 16 compound 15 (737392) for 48 hr. Compound 24 (742837) demonstrated no significant inhibition of either ROS production or NOX1 expression in HT-29 human colon cancer cells. Growth inhibitory properties of compound 3 (734958), a DTI analog, were similar to the parent compound.

Screening for NADPH Oxidase Isoform Specificity

DPI, DTI and 5 iodonium analog compounds were tested for specific inhibition of ROS produced by NOX1, NOX2, NOX4, NOX5, and DUOX2 in cellular models. To evaluate compound specificity, a luminescence assay for O2.- was used with HEK293 cells expressing all components of the NOX1 complex; fully differentiated HL-60 cells expressing active NOX2; and UACC257 melanoma cells that exclusively express active NOX5. H2O2 was measured by Amplex Red assay to determine NOX4 or Duox2 activity in fully reconstituted HEK293 cells. The method conducted was similar to the approach disclosed in Jaquet et al in Brit J. Pharmacology 164: 507-520, 2011 using somewhat different cell models for the NOX isoforms and we studied Duox2 in our own cell model. The results are set out in Table 2 Below.

TABLE 2

Inhibition of Isoform-Specific NADPH Oxidase-Dependent
ROS Production by Iodonium Analogs in Cell Models

| Compound | NOX Expression Model | | | | |
|---|---|---|---|---|---|
| | NOX1/ A1/O1 HEK 293 | NOX2 HL-60 | NOX4 HEK293 | NOX5 UACC-257 | DUOX2/A2 HEK 293 |
| 13 735294 (DPI) | 233 ± 122[¶] | 105 ± 55 | 880 ± 214 | 42 ± 27 | 6488 ± 1626 |
| 16 740104 | 70 ± 57 | 127 ± 20 | 161 ± 153 | 44 ± 21 | 4136 ± 1724 |
| 21 751140 | 249 ± 116 | 71 ± 15 | 127 ± 110 | 55 ± 20 | 1990 ± 1690 |
| 15 737392 | 357 ± 268 | 310 ± 53 | 139 ± 143 | 208 ± 129 | 225 ± 24 |
| 14 734428 | 136 ± 81 | 57 ± 35 | 260 ± 254 | 35 ± 21 | 412 ± 236 |
| 1 734426 (DTI) | 3413 ± 1601 | 1504 ± 1107 | 32253 ± 13780 | 3779 ± 2137 | No Inhibition |
| 3 734958 | 2217 ± 1211 | 1488 ± 646 | 29652 ± 41470 | 1200 ± 1116 | No Inhibition |
| 49 521 | 1019 ± 361 | 1470 ± 308 | 5533 ± 2681 | 229 ± 123 | 773 ± 362 |
| 24 742837 | 2522 ± 2414 | 4376 ± 999 | 35376 ± 42717 | 2094 ± 903 | No Inhibition |

[¶]nM IC$_{50}$ ± SE of 3-5 independent experiments

DPI, compounds 14, 16, 15, 21 (734428, 740104, 737392, or 751140) exposure for 30 min inhibited NOX1, 2, 4, and 5 with low nM IC50's; compounds 16, 14, 21 (740104, 734428, and 751140) were more potent inhibitors of NOX1, 2, and 4, respectively, than DPI; each was broadly active against these NOX isoforms. The DTI analog compound 3 (734958) was more potent than its parent molecule. Compound 15 and 14 (NSC737392 and 734428) were >10-fold more active than the other compounds examined against Duox2 (200-400 nM IC50's). These and compound 49 are at least a log more potent than the parent compound (DPI) for the inhibition of the colon cancer related oxidase DUOX2. These results show the novel iodonium analogs have anticancer activity that possesses enhanced potency against human NOX species, including the first agents with specificity against Duox2. Compound 49 (521) was prepared which shifted the nitro groups from the positions present in compound 15 (NSC737392) to the meta directing positions and caused the specificity toward NOX isoforms to shift. Compound 49 (521) has a much higher IC50 toward NOX1, 2, and 4 (which could be very useful in terms of NOT inhibiting the granulocyte/macrophage oxidase needed for host defense), while the inhibition of NOX5 and DUOX2 has remained about the same (submicromolar). Growth inhibition of NOX1-containing colon cancer cells (that require that oxidase to proliferate) by compound 49 (521) was also much less even at higher concentrations (versus the other analogs), supporting our NOX inhibition data.

Inhibition of HT-29 Human Colon Cancer Cell Growth: Clonogenic Assay

Several iodonium analog compounds were analyzed for inhibition of HT-29 growth using a clonogenic assay performed as described in Doroshow et al Biochem. Biophys. Res. Commun. 135: 330-335, 1986. The results for several compounds are provided in Table 3.

TABLE 3

Effect of iodonium analogs on clonogenic survival
of HT-29 human colon cancer cells

| Compound | IC$_{50}$ Concentrations for Different Drug Exposure Times (±SE) | | |
|---|---|---|---|
| | 2 hrs | 6 hrs | 10 days |
| 13 735294 (DPI) | 9.3 ± 3.9 µM | 799 ± 180 nM | ≈10 nM |
| 16 740104 | 1.2 ± 1.1 µM | 536 ± 635 nM | <10 nM |
| 21 751140 | ≈7 µM | 1.3 ± 0.3 7 µM | Not Tested |
| 15 737392 | 180 ± 157 nM | 116 ± 108 nM | <10 nM |
| 14 734428 | 77 ± 12 nM | 29 ± 23 nM | Not Tested |
| 1 734426 (DTI) | No Inhibition | 113.4 ± 92.3 µM | Not Tested |
| 3 734958 | No Inhibition | 91.2 ± 58.8 µM | Not Tested |

Taken together with Table 4 below, these data support different mechanisms of action (with respect to tumor cell growth inhibition) than DPI. I has been shown in Free Rad. Biol. Med. 57: 162-165, 2013 that DPI produces a G1 block as its mechanism of growth inhibition and does not cause apoptosis. In the new data, it is clearly confirmed that growth inhibition by DPI requires prolonged exposure, as would be the case for compounds that block cell cycle progression rather than inducing loss of overall clonogenic reproduction. On the other hand, for compound 15 737392 and compound 14 734428, which, from the table above require only a short exposure at nM concentrations to inhibit cell reproduction, it is likely that other cell kill mechanisms are at work. Compound 16 740104 is intermediate in this regard.

Effect on HT-29 Cell Cycle Progression

Several iodonium analog compounds were analyzed for effect on HT-29 cell cycle progression. The results are provided in Table 4.

TABLE 4

Iodonium analog treatment for 24 hours alters cell cycle progression
in HT-29 human colon cancer cells

| Compound | G1 (%) | | S phase (%) | | G2 (%) | |
|---|---|---|---|---|---|---|
| | 250 nM | 500 nM | 250 nM | 500 nM | 250 nM | 500 nM |
| HT-29 Untreated | 70.1 | 70.5 | 21.3 | 21.7 | 8.6 | 8.4 |
| 16 (740104) | 64.5 | 57.2 | 28.1 | 36.2 | 7.9 | 6.5 |
| 15 (737392) | 23.9 | 16.6 | 28.7 | 58.2 | 47.4 | 25.2 |
| 14 (734428) | 35.5 | 20.4 | 31.7 | 71.5 | 32.8 | 8.1 |

Compounds 14 and 15 cause a major block in cell cycle progression in S and G2 phases versus DPI (only G1 block, Free Rad. Biol. Med. 57: 162-165, 2013). These two compounds clearly kill cells after a short exposure, in other words they are cytotoxic, where DPI arrests cell growth without immediately killing them; DPI is cytostatic.

Example 3

A series of experiments using the Seahorse oxygen analyzer was conducted to determine IC50s for inhibition of mitochondrial respiration for comparison with NOX inhibitory concentrations. It was found in essentially every case, the NOX inhibitory concentration is at least 10 fold lower than that required to decrease respiration. These results both help in understanding the mechanism of action of the compounds, but also are important for predicting normal tissue, including cardiac myocyte, toxicity from these molecules.

The terms "a" and "an" do not denote a limitation of quantity, but rather denote the presence of at least one of the referenced item. The term "or" means "and/or". Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The modifier "about" used in connection with a quantity is inclusive of the stated value and has the meaning dictated by the context (e.g., includes the degree of error associated with measurement of the particular quantity).

The endpoints of all ranges directed to the same component or property are inclusive of the endpoints, are independently combinable, and include all intermediate points and ranges (e.g., ranges of "up to about 25 wt. %, or, more specifically, about 5 wt. % to about 20 wt. %," is inclusive of the endpoints and all intermediate values of the ranges of "about 5 wt. % to about 25 wt. %," such as about 10 wt. % to about 23 wt. %, etc.).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of treating a cancer, inhibiting tumor growth, or treating or preventing an inflammatory condition, comprising:
administering a therapeutically effective amount of a compound of Formulae Ie to a human patient or a non-human mammal in need thereof,

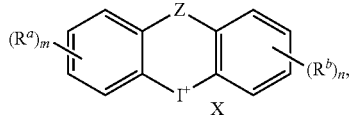

Formula Ie wherein
X is an anion;
Z is O, S, $CH_2$, —C(=O)—, or $NR^c$ where $R^c$ is hydrogen, $C_1$-$C_6$alkyl, $C_1$-$C_6$haloalkyl, or $C_2$-$C_6$alkanoyl;
wherein
when Z is S, —C(=O)—, or $NR^c$, each instance of $R^a$ and $R^b$ is independently hydroxyl, amino, cyano, substituted $C_1$-$C_6$alkyl, $C_2$-$C_6$alkenyl, $C_3$-$C_7$cycloalkyl, —CHO, —N($R^e$)$_2$, —CON($R^e$)$_2$, $C_1$-$C_6$alkoxy, $C_1$-$C_6$haloalkyl, $C_1$-$C_6$haloalkoxy, optionally substituted aryl, or optionally substituted heteroaryl, and
when Z is O or $CH_2$, each instance of $R^a$ and $R^b$ is independently hydroxyl, cyano, substituted $C_1$-$C_6$alkyl, $C_2$-$C_6$alkenyl, $C_3$-$C_7$cycloalkyl, —CHO, —CON($R^e$)$_2$, $C_1$-$C_6$alkoxy, $C_1$-$C_6$haloalkyl, $C_1$-$C_6$haloalkoxy, optionally substituted aryl, or optionally substituted heteroaryl,
where each substituted $C_1$-$C_6$alkyl of $R^a$ and $R^b$ is independently substituted with hydroxyl, halogen, amino, nitro, cyano, —COOR$^d$, —CHO, —N($R^e$)$_2$, —CON($R^e$)$_2$, $C_1$-$C_3$alkoxy, $C_1$-$C_3$haloalkoxy, $C_2$-$C_6$alkanoyl, —NHCO(CH$_2$)$_{1-2}$N($R^e$)$_2$,
where each $R^d$ is independently hydrogen or $C_1$-$C_3$alkyl,
where each $R^e$ is independently hydrogen, $C_1$-$C_6$alkyl, $C_2$-$C_6$alkanoyl, $C_1$-$C_6$haloalkyl, or fluorenylmethyloxycarbonyl ("Fmoc"),
where each optionally substituted aryl and optionally substituted heteroaryl can independently be substituted with halogen, hydroxyl, amino, nitro, cyano, $C_1$-$C_6$alkyl, $C_2$-$C_6$alkenyl, $C_3$-$C_7$cycloalkyl, $C_1$-$C_6$haloalkyl, —COOR$^d$, —CHO, —N($R^e$)$_2$, —CON($R^e$)$_2$, $C_1$-$C_3$alkoxy, $C_1$-$C_3$haloalkoxy, $C_2$-$C_6$alkanoyl, —NHCO(CH$_2$)$_{1-2}$N($R^e$)$_2$;
m is 0, 1, 2, 3, or 4; and
n is 1, 2, 3, or 4.

2. The method of claim 1, wherein X is a halide, an alkyl sulfonate, an aryl sulfonate, a phosphate, or a nitrate.

3. The method of claim 1, wherein X is chloride, bromide, iodide, $CH_3SO_3$—, $C_2H_5SO_3$—, $CF_3SO_3$—, 4-$CH_3C_6H_4SO_3$—, or $C_6H_5SO_3$—.

4. The method of claim 1, wherein m is 1 or 2 and n is 1 or 2.

5. The method of claim 1, wherein Z is O, $CH_2$, or $NR^c$ where $R^c$ is $C_1$-$C_6$alkyl, $C_1$-$C_6$haloalkyl, or $C_2$-$C_6$alkanoyl.

6. The method of claim 1, wherein Z is O, $CH_2$, or $NR^c$ where $R^c$ is $C_2$-$C_6$alkanoyl.

7. The method of claim 1, wherein Z is O.

8. The method of claim 1, wherein Z is $CH_2$.

9. The method of claim 1, wherein the cancer is colon cancer, kidney cancer (renal cell), melanoma, leukemia, prostate cancer, breast cancer, squamous lung cancer, ovarian cancer, pancreatic cancer, Non-Hodgkin lymphoma, or Glioblastoma Multiforme.

10. The method of claim 9, wherein the cancer is colon cancer.

11. A method of treating a cancer, inhibiting tumor growth, or treating or preventing an inflammatory condition, comprising:
administering a therapeutically effective amount of a compound of Formulae Ic to a human patient or a non-human mammal in need thereof,

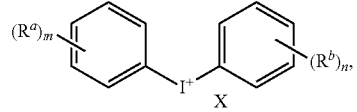

Formula Ic wherein
X is an anion;
each instance of $R^a$ and $R^b$ is independently hydroxyl, amino, cyano, substituted $C_1$-$C_6$alkyl, $C_2$-$C_6$alkenyl, $C_3$-$C_7$cycloalkyl, —CHO, —N($R^e$)$_2$, —CON($R^e$)$_2$, $C_1$-$C_6$alkoxy, $C_1$-$C_6$haloalkyl, $C_1$-$C_6$haloalkoxy, optionally substituted aryl, or optionally substituted heteroaryl,
where each substituted $C_1$-$C_6$alkyl can independently be substituted with hydroxyl, halogen, amino, nitro, cyano, —COOR$^d$, —CHO, —N($R^e$)$_2$, —CON($R^e$)$_2$, $C_1$-$C_3$alkoxy, $C_1$-$C_3$haloalkoxy, $C_2$-$C_6$alkanoyl, —NHCO(CH$_2$)$_{1-2}$N($R^e$)$_2$,
where each $R^d$ is independently hydrogen or $C_1$-$C_3$ alkyl,
where each $R^e$ is independently hydrogen, $C_1$-$C_6$alkyl, $C_2$-$C_6$alkanoyl, $C_1$-$C_6$haloalkyl, or fluorenylmethyloxycarbonyl ("Fmoc"),
where each optionally substituted aryl and optionally substituted heteroaryl can independently be substituted with halogen, hydroxyl, amino, nitro, cyano, $C_1$-$C_6$alkyl, $C_2$-$C_6$alkenyl, $C_3$-$C_7$cycloalkyl, $C_1$-$C_6$haloalkyl, —COOR$^d$, —CHO, —N($R^e$)$_2$, —CON($R^e$)$_2$, $C_1$-$C_3$alkoxy, $C_1$-$C_3$haloalkoxy, $C_2$-$C_6$alkanoyl, —NHCO(CH$_2$)$_{1-2}$N($R^e$)$_2$;
m is 0, 1, 2, 3, or 4; and
n is 1, 2, 3, or 4.

12. The method of claim 11, wherein X is a halide, an alkyl sulfonate, an aryl sulfonate, a phosphate, or a nitrate.

13. The method of claim 11, wherein X is chloride, bromide, iodide, CH$_3$SO$_3$—, C$_2$H$_5$SO$_3$—, CF$_3$SO$_3$—, 4-CH$_3$C$_6$H$_4$SO$_3$—, or C$_6$H$_5$SO$_3$—.

14. The method of claim 11, wherein m is 1 or 2 and n is 1 or 2.

15. The method of claim 11, wherein m is 1, 2, or 3 and n is 1, 2, or 3.

16. The method of claim 11, wherein m is 1, 2, 3, or 4 and n is 1, 2, 3, or 4.

17. The method of claim 11, wherein the cancer is colon cancer, kidney cancer (renal cell), melanoma, leukemia, prostate cancer, breast cancer, squamous lung cancer, ovarian cancer, pancreatic cancer, Non-Hodgkin lymphoma, or Glioblastoma Multiforme.

18. The method of claim 17, wherein the cancer is colon cancer.

19. A method of treating colon cancer, comprising:
administering a therapeutically effective amount of a compound of Formulae Ie to a human patient or a non-human mammal in need thereof,

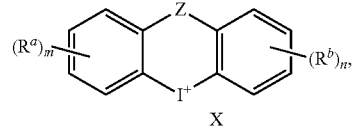

Formula Ie wherein
X is an anion;
Z is O, S, CH$_2$, —C(=O)—, or NR$^c$ where R$^c$ is hydrogen, $C_1$-$C_6$alkyl, $C_1$-$C_6$haloalkyl, or $C_2$-$C_6$alkanoyl;
each instance of $R^a$ and $R^b$ is independently hydroxyl, amino, cyano, substituted $C_1$-$C_6$alkyl, $C_2$-$C_6$alkenyl, $C_3$-$C_7$cycloalkyl, —CHO, —N($R^e$)$_2$, —CON($R^e$)$_2$, $C_1$-$C_6$alkoxy, $C_1$-$C_6$haloalkyl, $C_1$-$C_6$haloalkoxy, optionally substituted aryl, or optionally substituted heteroaryl,
where each substituted $C_1$-$C_6$alkyl of $R^a$ and $R^b$ is independently substituted with hydroxyl, halogen, amino, nitro, cyano, —COOR$^d$, —CHO, —N($R^e$)$_2$, —CON($R^e$)$_2$, $C_1$-$C_3$alkoxy, $C_1$-$C_3$haloalkoxy, $C_2$-$C_6$alkanoyl, —NHCO(CH$_2$)$_{1-2}$N($R^e$)$_2$,
where each $R^d$ is independently hydrogen or $C_1$-$C_3$ alkyl,
where each $R^e$ is independently hydrogen, $C_1$-$C_6$alkyl, $C_2$-$C_6$alkanoyl, $C_1$-$C_6$haloalkyl, or fluorenylmethyloxycarbonyl ("Fmoc"),
where each optionally substituted aryl and optionally substituted heteroaryl can independently be substituted with halogen, hydroxyl, amino, nitro, cyano, $C_1$-$C_6$alkyl, $C_2$-$C_6$alkenyl, $C_3$-$C_7$cycloalkyl, $C_1$-$C_6$haloalkyl, —COOR$^d$, —CHO, —N($R^e$)$_2$, —CON($R^e$)$_2$, $C_1$-$C_3$alkoxy, $C_1$-$C_3$haloalkoxy, $C_2$-$C_6$alkanoyl, —NHCO(CH$_2$)$_{1-2}$N($R^e$)$_2$;
m is 0, 1, 2, 3, or 4; and
n is 1, 2, 3, or 4.

* * * * *